United States Patent
Han et al.

(10) Patent No.: US 10,912,494 B2
(45) Date of Patent: Feb. 9, 2021

(54) SENSOR SIGNAL RECONSTRUCTION IN A SENSOR HUB

(71) Applicant: Intel Corporation, Santa Clara, CA (US)

(72) Inventors: Ke Han, Shanghai (CN); Dong Wang, Shanghai (CN); He Han, Shanghai (CN); Dror Lederman, Qiryat-Gat (IL); Lev Lavy, Misgav Dov (IL); Yehiel Shilo, Jerusalem (IL)

(73) Assignee: Intel Corporation, Santa Clara, CA (US)

( * ) Notice: Subject to any disclaimer, the term of this patent is extended or adjusted under 35 U.S.C. 154(b) by 264 days.

(21) Appl. No.: 15/780,226

(22) PCT Filed: Aug. 10, 2016

(86) PCT No.: PCT/IB2016/054835
§ 371 (c)(1),
(2) Date: May 30, 2018

(87) PCT Pub. No.: WO2017/109593
PCT Pub. Date: Jun. 29, 2017

(65) Prior Publication Data
US 2018/0353106 A1    Dec. 13, 2018

(30) Foreign Application Priority Data

Dec. 26, 2015   (WO) .................. PCT/IB2015/059994

(51) Int. Cl.
*A61B 5/11*   (2006.01)
*A61B 5/024*   (2006.01)
(Continued)

(52) U.S. Cl.
CPC .......... *A61B 5/1118* (2013.01); *A61B 5/0024* (2013.01); *A61B 5/02055* (2013.01);
(Continued)

(58) Field of Classification Search
CPC .......... A61B 2562/0219; A61B 5/0024; A61B 5/02055; A61B 5/02438; A61B 5/1118;
(Continued)

(56) References Cited

U.S. PATENT DOCUMENTS

2010/0097259 A1   4/2010   Zhang
2014/0140254 A1   5/2014   Nieminen et al.
(Continued)

FOREIGN PATENT DOCUMENTS

WO   2014120178 A1   8/2014

OTHER PUBLICATIONS

International Search Report and Written Opinion for PCT Patent Application No. PCT/IB2016/054835, dated Dec. 12, 2016, 15 pages.

*Primary Examiner* — John H Le
(74) *Attorney, Agent, or Firm* — Compass IP Law PC

(57) ABSTRACT

A sensor interface circuit enables signal reconstruction on data received from a sensor prior to sending the data to various sensor clients. Multiple sensor clients have different frequencies configured to receive sensor data. The sensor interface circuit performs signal reconstructions including data interpolation to generate interpolated data signal having frequencies corresponding to the different frequencies configured for the different sensor clients. Signal reconstruction can also include filtering the data. The sensor interface circuit sends the reconstructed data to the multiple clients in accordance with their different frequencies.

18 Claims, 12 Drawing Sheets

(51) Int. Cl.
 *A61B 5/00*    (2006.01)
 *A61B 5/0205*   (2006.01)
 *G06F 19/00*   (2018.01)
 *G16H 50/20*   (2018.01)
 *G16H 20/30*   (2018.01)

(52) U.S. Cl.
 CPC .......... *A61B 5/02438* (2013.01); *G06F 19/00* (2013.01); *A61B 2562/0219* (2013.01); *G16H 20/30* (2018.01); *G16H 50/20* (2018.01)

(58) Field of Classification Search
 CPC ........ G06F 19/00; G16H 20/30; G16H 40/40; G16H 40/67; G16H 50/20
 USPC ........ 702/14, 69, 75, 89, 104, 191; 341/155; 370/311; 707/770
 See application file for complete search history.

(56) References Cited

U.S. PATENT DOCUMENTS

| | | |
|---|---|---|
| 2014/0278116 A1 | 9/2014 | Halliday et al. |
| 2015/0169768 A1 | 6/2015 | Xu et al. |
| 2017/0122771 A1* | 5/2017 | Keal ..................... H04W 99/00 |
| 2017/0350919 A1* | 12/2017 | Bechhoefer ............. G01P 21/02 |

* cited by examiner

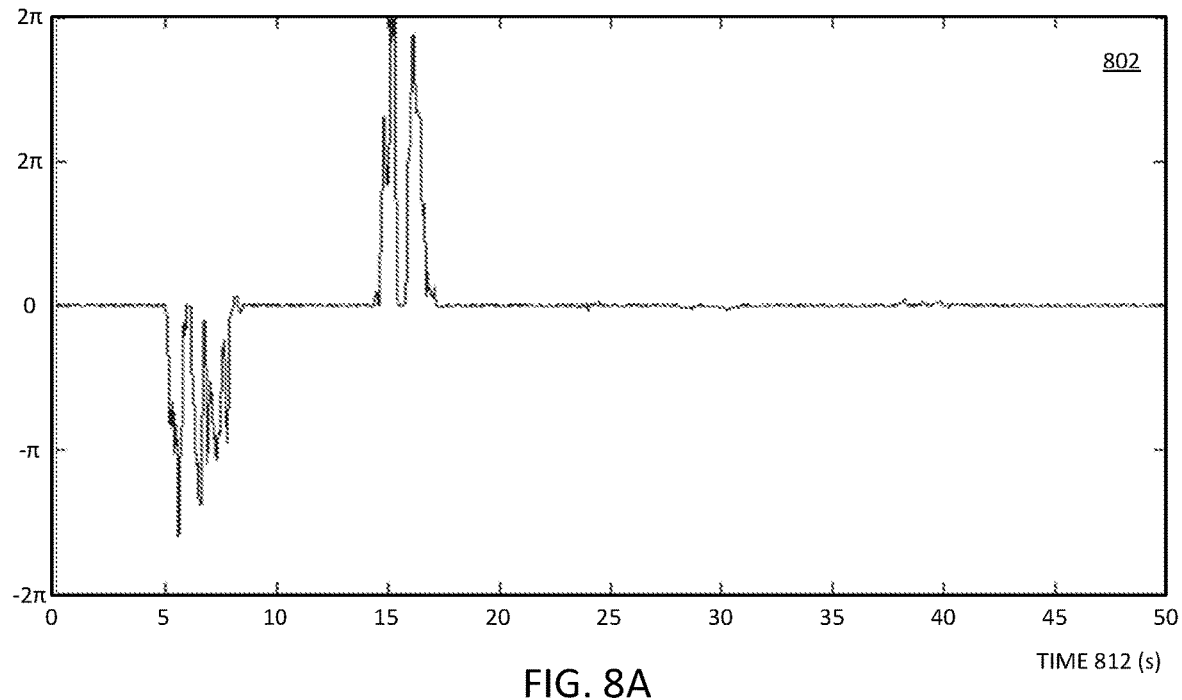

TABLE 820

| | DATA STREAM | STATIC NOISE (STD) | REDUCTION |
|---|---|---|---|
| 822 | 47 Hz RAW DATA | 0.101 DEG/s | N/A |
| 824 | 50 Hz MCF DATA | 0.100 DEG/s | 1.0% |
| 826 | 50 Hz INTERPOLATED DATA | 0.084 DEG/s | 17.3% |
| 828 | 50 Hz CLIENT FILTER DATA | 0.048 DEG/s | 52.5% |
| 830 | 50 Hz FIFO FILTER DATA | 0.070 DEG/s | 30.7% |
| 832 | 50 Hz BATCH FILTER DATA | 0.070 DEG/s | 30.5% |

FIG. 8C

TABLE 840

| | DATA STREAM | INTEGRATION RESULT | DRIFT IN TIME |
|---|---|---|---|
| 842 | 47 Hz RAW DATA | -2.32 | BASELINE |
| 844 | 20 Hz MCF DATA (IGNORE TIMESTAMP) | 4.65 | 0.58 DEG/MIN |
| 846 | 20 Hz MCF DATA (CONSIDER TIMESTAMP) | -1.66 | 0.06 DEG/MIN |
| 848 | 20 Hz INTERPOLATED DATA | -1.90 | 0.04 DEG/MIN |
| 850 | 20 Hz CLIENT FILTER DATA | -2.63 | 0.03 DEG/MIN |
| 852 | 20 Hz FIFO FILTER DATA | -2.10 | 0.02 DEG/MIN |
| 854 | 20 Hz BATCH FILTER DATA | -2.00 | 0.03 DEG/MIN |

…

SENSOR SIGNAL RECONSTRUCTION IN A SENSOR HUB

CLAIM OF PRIORITY

This application is a U.S. National Phase application under 35 U.S.C. § 371 of International Application No. PCT/IB2016/054835 filed Aug. 10, 2016, entitled "SENSOR SIGNAL RECONSTRUCTION IN A SENSOR HUB", which in turn is based on PCT/IB2015/059994, entitled, "SENSOR SIGNAL RECONSTRUCTION IN A SENSOR HUB" the entire contents of which are incorporated herein by reference. The present application claims the benefit of priority of these applications.

FIELD

Descriptions relate generally to sensors, and certain descriptions relate more particularly to power management of an activity monitoring system.

COPYRIGHT NOTICE/PERMISSION

Portions of the disclosure of this patent document may contain material that is subject to copyright protection. The copyright owner has no objection to the reproduction by anyone of the patent document or the patent disclosure as it appears in the Patent and Trademark Office patent file or records, but otherwise reserves all copyright rights whatsoever. The copyright notice applies to all data as described below, and in the accompanying drawings hereto, as well as to any software described below: Copyright © 2015, Intel Corporation, All Rights Reserved.

BACKGROUND

Many electronic devices include sensors to measure environmental conditions. Such sensors can detect motion, orientation, temperature, and/or other conditions. Many services and capabilities of electronic devices are based on sensor data. As more services and capabilities are added to electronic devices/computing devices, the number of services based on sensor data increases. When multiple services rely on the same sensor type for data, multiple redundant sensors could be included in the device, but adding more sensors increases space and power needs, and increases device costs. Thus, solutions have arisen that provide sensor data from a single physical sensor to multiple sensor clients that each need data from the same sensor.

However, different sensor clients have different sampling frequencies associated with them, depending on the feature or service provided. Commonly a sensor hub is connected to the sensors, and arbitrates and distributes data to the sensor clients. The sensor hub has two conflicting goals with respect to distributing the sensor data: first, the data should be accurate, which is best achieved by distributing data in accordance with a specific client's requested sampling frequency; and, second, the sensor hub should operate in a power-efficient manner. Typically, increased accuracy comes at the cost of increased power. Conversely, power efficiency has traditionally come at the cost of lower data accuracy.

Two previous sensor management approaches illustrate the conflict. The LCM (least common multiple) method determines the least common multiple of all client frequencies, and samples the sensor at the LCM. The LCM method distributes data right on time, but is not low power due to its tendency to sample at a faster rate than any requested frequency of a client. The MCF (maximum client frequency) method operates the physical sensor operate at the highest frequency requested of any of the clients. In practice, the actual sampling frequency may be different than what can be achieved with an on-device oscillator, which means the data is not perfectly accurate. Additionally, when lower-frequency clients request data at rates that are not factors of the highest frequency, the sensor hub provides only the closest previous data sample available. Thus, the input frequency changes intervals with respect to the actual data, and the sampled data does not necessarily reflect the current sensor condition. MCF is therefore lower power than LCM, but is not as accurate. Thus, traditionally a sensor hub cannot provide a low power, accurate data stream to sensor clients.

BRIEF DESCRIPTION OF THE DRAWINGS

The following description includes discussion of figures having illustrations given by way of example of implementations of embodiments of the invention. The drawings should be understood by way of example, and not by way of limitation. As used herein, references to one or more "embodiments" are to be understood as describing a particular feature, structure, and/or characteristic included in at least one implementation of the invention. Thus, phrases such as "in one embodiment" or "in an alternate embodiment" appearing herein describe various embodiments and implementations of the invention, and do not necessarily all refer to the same embodiment. However, they are also not necessarily mutually exclusive.

FIG. 8A is a diagrammatic representation of a graph of test data for a gyroscope of a system including a sensor hub that performs sensor signal reconstruction.

FIGS. 8B-8C are diagrammatic representations of tables showing experimental results for one embodiment of a system that performs sensor signal reconstruction.

Figure 1:
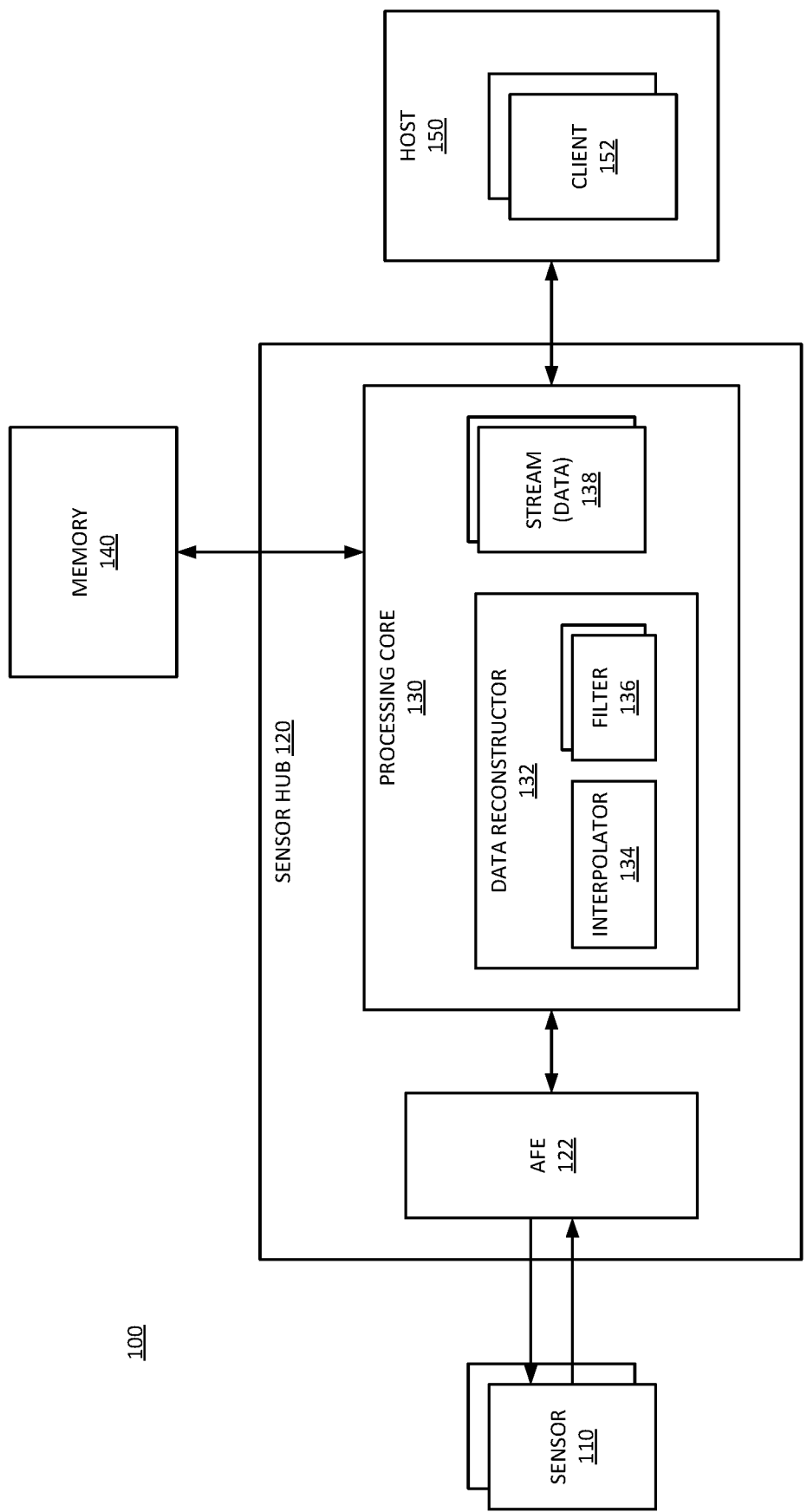
FIG. 1 is a block diagram of an embodiment of a system with a data reconstructor in a sensor hub.

Descriptions of certain details and implementations follow, including a description of the figures, which may depict some or all of the embodiments described below, as well as discussing other potential embodiments or implementations of the inventive concepts presented herein.

DETAILED DESCRIPTION

As described herein, a sensor interface circuit enables signal reconstruction on data received from a sensor prior to sending the data to various sensor clients. The sensor interface circuit can provide accurate streams of sensor data to multiple sensor clients having different frequencies, while conserving power compared to previous methods that provide accurate sensor data. The sensor interface circuit performs signal reconstruction including data interpolation to generate interpolated data signals having frequencies corresponding to the different frequencies configured for the different sensor clients. In one embodiment, signal reconstruction includes filtering the data. The sensor interface circuit sends the reconstructed data to the multiple clients in accordance with their different frequencies. Thus, the sensor interface described herein enables lower power sensor management while improving signal quality to the sensor clients.

In one embodiment, the sensor interface is or includes a sensor hub, which connects one or multiple sensors to one or more clients. The sensor hub can include one or more processing components to perform signal reconstruction of a sensor signal for distribution as signal streams to clients having different frequency requirements. In one embodiment, the sensor hub interfaces with the physical sensor in accordance with a maximum client frequency (MCF) or the frequency of the client with the highest frequency requirement. Thus, the sensor hub can sample the sensor in accordance with the MCF. Instead of passing the raw sensor data or the data that was sampled from the sensor, the sensor hub performs interpolation to reconstruct or generate sensor signals associated with required frequency and timestamp settings.

In one embodiment, the sensor hub performs one or more types of filtering and/or other data processing on the data in addition to the interpolation. It will be understood that the sensor hub can perform interpolation before and/or after filtering or other data processing. In one embodiment, the sensor hub performs anti-jitter processing on the data as part of signal reconstruction. In one embodiment, the sensor hub takes advantage of one or more delays that already exist in the system for downsampling and/or for buffering to perform noise filtering without adding delay. For example, the system can apply appropriate filters during one or more of the inherent delay in sensor hub downsampling, input FIFO (first in, first out) buffer, and batch modes, applying suitable filter to reduce sensor noise without adding any extra delay.

With interpolation processing, the sensor hub can operate and monitor the physical sensor only at the highest frequency required by the sensor clients, and does not need to operate the sensor at a multiple of any given sensor client frequency. However, instead of providing a closest available sample as the data for a client, the sensor hub can compute an estimated data for the exact timing requested. With filter processing, the sensor hub can provide a sensor signal with improved signal quality than the raw data. Traditional sensor systems provide raw data to the sensor clients, which each apply processing to the raw data. The clients would perform processing because there are not concerns about time constraints. However, the fact that each client would separately process the data increases the overall amount of processing performed on the data as compared to what is described herein. Thus, a sensor interface that performs interpolation and can selectively perform filtering can provide better data to the sensor clients.

FIG. 1 is a block diagram of an embodiment of a system with a data reconstructor in a sensor hub. System 100 includes elements of a computing device, such as a handheld electronic device, portable computer, or other system that includes sensors to measure physical or environmental conditions or states. Sensor 110 represents one or more sensors in system 100 that monitor the physical or environmental conditions or the condition or state in which system 100 currently is. The condition or state measured by sensor 110 can be generically referred to here as an environmental condition.

Sensor 110 can be or include an accelerometer, a gyroscope, a magnetometer, a global positioning system (GPS), barometer, temperature sensor, humidity sensor, light sensor, heart rate sensor, and/or other sensor that generates streaming sensor data. Sensor 110 can include a discrete sensor device coupled to sensor hub 120. In one embodiment, sensor 110 is a sensor circuit integrated onto a hardware platform shared with sensor hub 120, and can be, for example, within the same packaging as sensor hub 120. Sensor 110 can monitor conditions continuously and/or periodically, with high frequency periods generating data that is functionally equivalent to continuous. Sensor 120 generates raw data, which refers to a value of the sensor at a point when it is sampled, and can be an analog or digital measurement.

Sensor hub 120 represents circuitry to receive the raw data from sensor 110. Sensor hub 120 can be or include an ASIC (application specific integrated circuit), mixed signal circuitry to process digital and analog signals, one or more processors such as a microcontroller unit, coprocessor, digital signal processor (DSP), programmable logic unit (PLU), and/or other circuitry. In one embodiment, sensor hub 120 includes multiple discrete components or circuits. In one embodiment, sensor hub 120 is a system on a chip (SoC) device. Sensor hub 120 can offload sensor signal processing operations from a central processing unit (CPU) of a computing device in which system 100 is incorporated. Sensor hub 120 can be designed and configured to be more power efficient for interfacing with sensor 110 relative to the CPU, which can save power consumption while simultaneously providing improved performance.

In one embodiment, sensor 110 generates a digital output that can be received and processed directly by sensor hub 120. In such a case, sensor hub 120 can include an interface circuit that interfaces with digital signals. In one embodiment, one or more sensors 110 generate an analog output. In one embodiment, sensor hub 120 includes AFE (analog frontend) 122, which can convert the analog signals into digital signals for processing by processing core 130. In one embodiment, AFE 122 receives both analog and digital signals. AFE 122 can include receivers, drivers, input termination, multiplexers, and/or other logic or circuits to interface with one or more sensors 110. Whether it is AFE 122 and/or circuitry or hardware in addition to AFE 122, sensor hub 120 includes and/or is a sensor interface circuit to interface with one or more sensors 110. The interface includes appropriate input/output (I/O) hardware such as pins, connectors, signal lines, and/or other hardware in addition to transceivers and termination hardware. The I/O hardware enables sensor hub 120 to receive sensor data from sensor 110 (the arrow pointing from sensor 110 to sensor hub 120) and to send data (such as configuration data) to sensor 110 (the arrow pointing from sensor hub 120 to sensor 110).

Sensor hub 120 includes processing core 130, which represents logic resources to execute operations and process activity data received from sensor 110. Processing core 130 represents the computational core logic of sensor hub 120. In one embodiment, processing core 130 can represent a combination of hardware logic and programming to provide processing functionality within sensor hub 120. Thus, the circuitry of sensor hub 120 can include direct-coded and/or software controlled hardware or a combination. In one embodiment, processing core 130 includes multiple execution blocks to perform the processing of sensor data.

System 100 includes memory 140 to store code and/or data values for operations of sensor hub 120. Memory 140 can include volatile memory resources (memory whose state is indeterminate if power is interrupted) and/or nonvolatile memory resources (memory that maintains determinate state even if power is interrupted). Memory 140 can also include registers or other storage mechanisms within system 100. In one embodiment, memory 140 is included within sensor hub 120 or at least a portion of memory resources 140 is included within sensor hub 120. In one embodiment, sensor hub 120 represents an integrated sensor hub (ISH) that integrates processing and memory for multiple different sensors. In one embodiment, sensor hub 120 is incorporated into a device or SoC of a host processor in a computing device where the host processor executes a host operating system that controls the computing device. In one embodiment, sensor hub 120 is separate from the host processor. In one embodiment, memory 140 is integrated into an SoC that includes sensor hub 120.

System 100 includes host 150, which represents a host platform to which sensor hub 120 interfaces sensors 110. Thus, host 150 is a consumer of sensor data, and sensor hub 120 provides the sensor data to the host. Host 150 can include one or more software agents executing on a host processor or CPU of a computing device that incorporates system 100. Client 152 represents one or more agents that receive and use sensor data. In one embodiment, client 152 can be part of an application or a service that executes under a host operating system. In one embodiment, client 152 is a service or background application that executes as part of the host operating system and/or an application.

Traditionally, all clients 152 would perform all processing on raw sensor data. Thus, one or more sensors 110 would generate sensor data, which was sampled and distributed by sensor hub 120 to clients 152. Clients 152 would then perform all processing on the sensor data. Thus, any filtering of the data was performed by the client to ensure timing was correct, and so sensor hub 120 did not introduce delay by filtering the data.

Sensor hub 120 includes data reconstructor 132, shown as part of processing core 130. Data reconstructor 132 represents circuitry or logic to perform processing on the sensor data prior to sending the sensor data to clients 152. Traditionally the timestamping and timing of data samples of data delivered by sensor hub 120 to clients 152 could not be guaranteed to match the frequency requirements of client 152. In one embodiment, data reconstructor 132 includes interpolator 134 to perform interpolation processing or provide interpolation services on sensor data. In one embodiment, interpolator 134 performs linear interpolation. In one embodiment, interpolator 134 performs polynomial or spline interpolation. In one embodiment, other known types of interpolation can be modified to be applied by interpolator 134. In most cases tested by the inventors, linear interpolation was determined to provide results of adequate quality for the desired performance characteristics. Such desired performance characteristics can include percentage errors to comply with standards or guidelines for specific types of computing devices (such as requirements for smartphone devices). Linear interpolation may not be adequate for other desired performance characteristics.

In one embodiment, data reconstructor 132 includes one or more filters 136. Filter 136 represents an algorithmic processing operation that removes certain data and/or enhances (e.g., amplifies) other data. Typically filtering operations can include attenuating signal contributions for certain ranges of frequencies and/or for frequencies above and/or below a threshold frequency. Thus, filtering operations can include operations performed to enhance the signal to noise ratio for desired frequency ranges, where frequencies outside the desired range are considered noise. Algorithmic processing can include processing by hard-coded circuitry. Algorithmic processing can include processing by coded logic to cause a processor to operate in accordance with desired mathematical operations.

In one embodiment, processing core 130 includes one or more data streams 138. Data stream 138 represents a series of data values or processed samples that are based on the raw data received from sensor 110. Data stream 138 includes interpolated values from interpolator 134, which can guarantee the timing of data sample points for clients 152 in accordance with the frequency requirements of the specific client 152. In one embodiment, one or more data streams 138 includes filtered data sample points for one or more clients 152, based on operation of one or more filters 136. In one embodiment, data reconstructor 132 applies different filters 136 for different clients 152. In one embodiment, data reconstructor 132 applies a series of filters 136 to all data streams 138 for clients 152. There can be, for example, one or more filters 136 applies to all data streams 138, and selective additional filters 136 applied to the already filtered data streams 138 for specific clients 152. Thus, system 100 is flexible to provide interpolated and filtered data for clients 152.

In one embodiment, data reconstructor 132 applies filters 136 during natural periods of delay within the data distribution to clients 152. By applying filtering during periods of existing delay, data reconstructor 132 can apply filtering without introducing additional latency into data streams 138. As discussed in more detail below, the existing delays can include buffering delays and sampling delays. Such buffering and/or sampling delays can be in accordance with the data desired for specific clients 152, and thus be existing as a natural delay in providing sensor data from sensor 110 to client 152.

Thus, it will be understood that sensor hub 120 includes hardware to couple or connect to one or more sensors 110 and receive sensor data. Sensor hub 120 includes processing hardware including processing core 130 to process the received sensor data. Sensor hub 120 includes data reconstructor to perform signal reconstruction on the sensor to generate one or more data streams 138. The signal reconstruction includes data interpolation of sensor data values to generate interpolated data streams 138 having different frequencies corresponding to different frequencies configured for different sensor clients 152. In one embodiment, the signal reconstruction includes filtering. Sensor hub 120 provides the processed or reconstructed data to the multiple clients in accordance with their configured frequencies.

Consider an embodiment of system 100 where interpolator 134 includes a linear interpolator and filter 136 includes at least one FIR (finite input response) filter, and at least one IIR (infinite input response) filter. Linear interpolator 134 can provide adequate performance for certain cases while having a small computational footprint. Thus, the computation time and power required are lower than other types of interpolation. If linear interpolator 134 performs only integer operations, the computation time and processing power required can be negligible relative to overall system power budget.

Where filter 136 includes a FIR filter of order N, there are only N+1 multiply and N add operations in the computation of the filtering. N can be selected to also result in negligible computation time and power relative to overall operation. In one embodiment, one N order FIR filter contains N+1 filter parameters, which can be stored in memory 140. Suppose system 100 includes 4 filters (having normalized cutoff frequencies of: 0.2, 0.4, 0.6, 0.8) with order 30, and 4 filters with order 10. Such a system has a total data size that is still very small, seeing that (4*31+4*11)*2 Bytes=0.33 KB.

When filter 136 includes an IIR filter of order N, there are 2N+1 multiply and 2N add operations in the computation of the filtering. Again, N can be selected to result in computation time and power that is reasonable for the power budget and timing constraints of system 100. For such an IIR filter, in one embodiment, one N order IIR filter contains 2N+1 filter parameters. Suppose system 100 includes 5 filters (having normalized cutoff frequencies of: 0.1, 0.2, 0.3, 0.4, 0.5), with order 10, 5, 3, 2, the total data size is about (2*10+1+2*5+1+2*3+1+(2*2+1)*2)*2 Bytes=0.10 KB. The amount of storage for each filter is small relative to modern memory sizes, and can perform computations within timing constraints of system 100.

The described embodiment of system 100 where interpolator 134 includes a linear interpolator and filter 136 includes at least one FIR filter, and at least one IIR filter, and/or another embodiment of system 100 with a different configuration, can provide performance advantages over traditional sensor interfacing.

System 100 is power efficient by enabling lower frequency sampling of sensor 110 relative to traditional approaches. In one embodiment, sensor hub 120 operates sensor 110 at the MCF. Despite the slower sampling, system 100 provides accurate sampling for all clients 152, seeing that sensor hub 120 performs data reconstruction with interpolator 134. Interpolator 134 also enables perfect timestamping for samples for each client, regardless of what frequency the client requests. Additionally, interpolation enables sensor hub 120 to provide data samples with correct timing without depending on the oscillator frequency of the sensor hub. While not specifically shown, it will be understood that sensor hub 120 performs its operations based on the clock timing of a reference oscillator. In traditional systems, the ability of the sensor hub to meet client timing requirements was dependent on the oscillator frequency, with some client frequencies not being perfectly divisible by the sensor hub oscillator frequency. With interpolation, the sensor hub reference oscillator frequency does not constrain sensor hub 120 from providing accurate and timely data samples. It will be understood that interpolated data samples are estimates rather than exact representations of the sensor data, but testing has determined that interpolation can provide data samples having low enough error to provide a sensor interface that operates within desired performance parameters.

In one embodiment, filter 136 includes processing for jitter removal and noise reduction. Traditionally, jitter removal and noise reduction have been solely performed within clients 152. In one embodiment, system 100 can perform jitter removal and noise reduction without introducing additional delay. For example, sensor hub 120 can include existing modes for downsampling, FIFO buffering, batch buffering, and/or other modes. Such modes have inherent delays, which sensor 120 can use to apply one or more filters 136.

Figure 2:
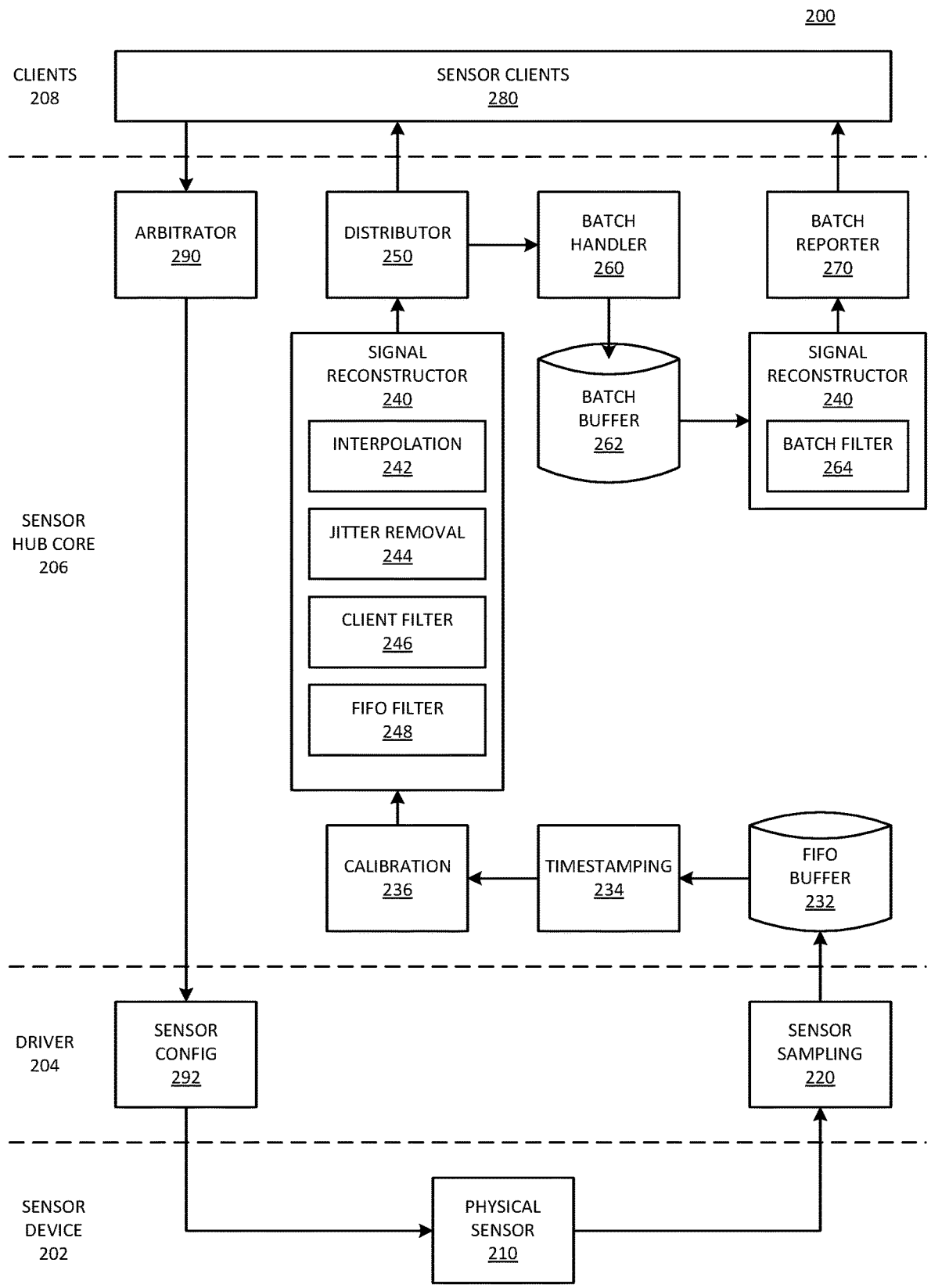
FIG. 2 is a block diagram of an embodiment of a system that performs data reconstruction in a sensor hub.

FIG. 2 is a block diagram of an embodiment of a system that performs data reconstruction in a sensor hub. System 200 illustrates elements of a sensor interface system, with sensor device 202 that generates data, and clients 208 as clients for the data. Sensor hub core 206 and driver 204 can provide the interface for clients 208 to obtain data from sensor device 202. System 200 is one example of an embodiment of system 100. As such, sensor device 202 can be an example of sensor 110, sensor core 206 and driver 204 can be one example of components of sensor hub 120, and clients 208 can be one example of clients 152. System 200 is illustrated hierarchically based on flow of sensor data from its creation by physical sensor 210 to processing in sensor core 206 to distribution to sensor clients 280.

System 200 can be thought of as several levels of a sensor interface system. At a lowest level is the level of sensor device 202. For purposes of simplicity, one physical sensor 210 is illustrated, but multiple sensor devices can be included, and each can have different clients, different sampling rates, different interface settings (e.g., for interface hardware), and/or different operation than other sensors. In one embodiment, system 200 can interface with multiple different sensors 210 and apply the interpolation and/or filtering and/or other processing on the signals from such sensors. Sensor device 202 can be or include a gyroscope, accelerometer, magnetometer, a barometer, a temperature sensor, a humidity sensor, a light sensor, a heart rate sensor, and/or other streaming sensor.

At the next level is the level of driver 204. Driver 204 includes hardware to control the physical interface to sensor 210. Thus, different timing and configuration parameters that make up settings for the physical interface are controlled by driver 204. It will be understood that outfacing driver settings configure the settings of the physical sensor itself, while inward-facing driver settings configure the hardware interface of the sensor hub to obtain data from the physical sensor.

At the next level is the level of sensor hub core 206. Sensor hub core 206 includes processing hardware to receive and process data from physical sensor 210. Sensor hub core 206 as described herein performs interpolation and/or other signal processing to prepare the raw data into data streams for delivery to the sensor clients. It will be understood that such processing can be distinguished from systems in which a preprocessor is used to perform preliminary analysis on the data to determine if the main processor should receive the data. Rather, the processing herein reconstructs a data stream from the raw sensor data to generate data for sending to the main processor and the clients or agents that execute on the main processor.

At the highest level is the level of clients 208. Clients 208 process or otherwise apply or use sensor data to provide functionality for a computing device in which system 200 is incorporated. For example, in a case where physical sensor 210 is an accelerometer, clients 208 can refer to any application or process executing on a host computing device that uses motion data. Sensor clients 280 can include host applications (either operating system or application level agents) or sensor hub virtual or abstract sensors that require physical sensor streaming data from the sensor core.

Physical sensor 210 generates sensor data identifying a condition or a change of a condition. The sensor hub includes sensor sampling 220 to sample the sensor data. Sensor sampling 220 can include multiple associated configuration settings that enable the sensor hub to obtain the data from sensor 210. In one embodiment, the sensor hub receives the sensor data samples and queues them in a first in, first out (FIFO) buffer. FIFO buffer 232 can buffer a short period of raw data, and send it to a client in a package, instead of sending data on each separate sample. In one embodiment, the length of FIFO buffer 232 is on the order of 10-100 entries, although different lengths can be used.

In one embodiment, the sensor hub buffers sensor input data. The application of buffers in the sensor system can provide power saving in the sensor hub. In one embodiment, settings in driver 204 for sensor sampling 230 configure the use of FIFO buffer 232. In one embodiment, FIFO buffer 232 allows sensor physical sensor 210 to report data in a buffer instead of as a single report. In one embodiment, the sensor buffers its generated sensor data and sends it in a package instead of one sample at a time. In one embodiment, the sensor hub waits until FIFO buffer 232 is full or has reached a threshold number of entries, and then accesses the data for processing. In one embodiment, a sensor hub includes multiple FIFO buffers, which can include one or more buffers per physical sensor 210. In one embodiment, FIFO buffer 232 is an internal buffer inside the sensor hub that receives one or more samples or values from physical sensor 210. FIFO buffer 232 can be considered part of a data path from the physical sensor to the sensor client.

In one embodiment, the sensor hub includes timestamping 234 to add timestamping to the raw sensor data. Timestamping includes associating time information with the data samples. The timestamp can refer to a digital value representing an absolute time, or a relative time from an offset. The timestamping data can be metadata recorded with the data samples. In one embodiment, the sensor hub includes calibration 236 to perform axis remapping and/or other calibrations such as offset calibration.

The sensor hub includes signal reconstructor 240 to perform processing on raw sensor data. Signal reconstructor 240 includes interpolation 242. Signal reconstructor 240 provides signal reconstruction in the sensor hub, to provide processed data or reconstructed data instead of providing the raw data to the client. In one embodiment, signal reconstructor 240 includes jitter removal 244. In one embodiment, signal reconstructor 240 includes one or more filters, such as client filter 246, FIFO filter 248, or batch filter 264. In one embodiment, the sensor hub includes naturally existing sampling delays. The existing sampling delays can include the following.

In one embodiment, multiple different sensor clients 280 have different associated frequencies. There can be delay associated with the sampling for the different associated frequencies, and specifically for downsampling from a higher frequency to a lower frequency. For example, one client may request data from physical sensor be delivered at 50 Hz, and another at 10 Hz. As such, the sensor hub can sample physical sensor 210 at 50 Hz for the one client, and downsample the data to 10 Hz data for the other client. When data does not need to be downsampled, the client can be presumed to want all the frequency information in the sample. When the client wants the data at a lower frequency, the client can be assumed to want lower frequency information, and the downsampled data can be filtered for the desired information. The more downsampling, the more frequency information that can be removed. Thus, more downsampling corresponds with more delay and more frequency information to be filtered out. In one embodiment, the sensor hub can use the downsampling delay to apply client filter 246. For example, downsampling from 50 Hz to 10 Hz provides a natural delay of 5 samples, which works out to 0.1 second.

In one embodiment, FIFO input buffer 232 introduces delay by queuing data samples from physical sensor 210. The application of buffering allows delay in reporting the data to the subsequent component, which allows both components to have longer idle periods between reporting activities. The number of samples buffered determines the delay. Input buffers typically includes somewhere on the order of tens to hundreds of samples. In one embodiment, batch buffer 262 introduces delay be queuing multiple groups of samples into a batch to deliver a larger group of samples to a client. In both cases, buffering allows some delay in reporting data, with the introduction of delay justified by power saving. In one embodiment, the sensor hub performs filtering during the delays introduced by the buffering.

Interpolation 242 enables the sensor hub to reconstruct sensor streaming from the raw data. Interpolation 242 allows the sensor hub to fit different frequency requirements for sensor clients 280. In one embodiment, interpolation 242 includes linear interpolation. In one embodiment, the algorithmic expression for operations of interpolation 242 can stated as follows:

$$data_t = \frac{(t1-t0)(data_{t1}-data_{t0})}{t1-t0+t} + data_{t0}$$

In the expression, $data_t$ is the data sample at time t, and $data_{t1}$ and $data_{t0}$ are previous data samples. The times t1 and t0 correspond to the times of the other samples. It will be observed that in the algorithmic expression, all calculations are integer operations, which results in minimal computation costs.

In one embodiment, signal reconstructor 240 includes jitter removal 244 to remove jitter in sensor streaming. Jitter removal 244 can be considered in one embodiment to be a data filter or jitter removal filter. In one embodiment, jitter removal can be implemented as a series of integer calculations. It will be understood that the system should implement a lower frequency limit to jitter removal, seeing that frequencies below the threshold can actually be desired sensor data. For example, for an accelerometer sensor and/or other sensor device used to monitor user activity/movement, the system should not remove frequencies lower than double a signal frequency that can indicate user movement. The cutoff for user movement is somewhere in the range of 15-25 Hz. Thus, such a system may impose a limit of 50 Hz signals for jitter removal to avoid removing a frequency signal generated from user motion (such as tapping, which can generate signals around 25 Hz). In one embodiment, jitter removal 244 detects and removes jitter by comparing data samples with neighboring samples.

The number of neighbor samples to compare can be set by configuration for the system, depending on amount of time available to process, and determination of accuracy needed for jitter removal. For example, either of the following could be used to detect jitter, with other similar variations possible:

$$abs(2d_k - d_{k-1} - d_{k+1})/2 >> abs(d_{k-1} - d_{k+1})$$

$$abs(4d_k - d_{k-1}d_{k-2} - d_{k+1} - d_{k+2})/4 >>$$

$$abs(d_{k-1}d_{k+1}) + abs(d_{k-1} - d_{k-2}) + abs(d_{k+2} - d_{k+1})$$

In the expressions, abs( ) is a function to take the absolute value. The values of $d_{ki}$ represent data sample points, with k being the present sample, and the other samples indicating preceding (e.g., k−1) or succeeding (e.g., k+1) samples. It will be observed that in general the function determines if a multiple of the present sample (e.g., either 2 times $d_k$ or 4 times $d_k$, depending on how many neighboring samples are compared) minus the samples is much greater than the value of the samples subtracting from each other. The mathematical expression '>>' can refer to an engineering rule of thumb of approximately 5 times more or ten times more, depending on configuration of the system. The configuration should account for likelihood of the signal to vary, and time between samples. It will be understood that a data value that significantly varies (is >> than neighboring values) is likely an aberration and can be treated as jitter, and eliminated.

In one embodiment, signal reconstructor 240 includes one or more filters to apply to generate one or more filtered data streams for one or more clients. In one embodiment, signal reconstructor 240 applies different filters for different clients. In one embodiment, signal reconstructor 240 applies different filters in series, and sends the data to certain clients prior to performing additional processing with additional filters. In one embodiment, signal reconstructor 240 includes multiple versions of the same filter. Such different versions of the filter can be applied based on system conditions. For example, signal reconstructor 240 can apply one version of a filter based on the type of sensor being read, based on a configuration setting, based on a signal threshold detected, or other condition. For example, sensor hub core 206 can apply different filters based on different I/O configuration settings of sensor sampling 220.

In one embodiment, signal reconstructor 240 includes client filter 246 to reduce noise during client downsampling. For example, consider downsampling from a 50 Hz raw data signal to a data stream for a 20 Hz client, the additional time used to record samples that are not needed by the 20 Hz client can be used to reduce noise in 20 Hz sensor streaming. For example, in one embodiment, client filter 246 applies a low pass filter on the 50 Hz data to produce a better 20 Hz data stream for a 20 Hz client. In one embodiment, client filter 240 is or includes an IIR filter. Other filter types can be used. One example of a mathematical expression that can be implemented by client filter 246 follows:

$$data_{IIRt} = \sum_{k=1}^{N+1} B_k data_{t-k+1} - \sum_{k=2}^{N+1} A_k data_{IIR(t-k+1)}$$

The IIR filter example above is an N order filter, where N sets the number of iterations to use in the filtering. $B_k$ and $A_k$ represent coefficients that can be used to weight or normalize the data. It will be understood that to apply the filtering during downsampling, there may be varying window sizes in which to apply filtering, depending on how much a signal is downsampled. Thus, in one embodiment, signal reconstructor 240 includes multiple different IIR filters from which to select, such as filters of order 10, 5, 3, and 2, which can have different versions based on different cutoff frequencies (e.g. five different cutoff frequencies for each N order filter, which cutoff frequencies could be normalized as 0.1, 0.2, 0.3, 0.4, and 0.5).

In one embodiment, signal reconstructor 240 includes FIFO filter 248 to remove high frequency noise during an input buffering delay. In one embodiment, the FIFO buffer can be of different lengths, and different filter orders can be stored to accommodate different buffer lengths. In one embodiment, FIFO filter 248 is or includes a FIR filter. Other filter types can be used. In one embodiment, signal reconstructor 240 includes multiple different FIFO filters 248 which can be selected to process data. As an example, consider multiple filters selected from any combination of order 30, order 20, and order 10, with normalized cutoff frequencies of 0.2, 0.4, 0.6, and 0.8. While some buffers may have sufficient length to apply a filter of an order higher than 30, experimental results have shown that order 30 generates sufficient performance for implementation in common commercial mobile devices. One example of a mathematical expression that can be implemented by FIFO filter 248 follows:

$$data_{FIRt} = \sum_{k=1}^{N+1} B_k data_{(t-k+1)}$$

Sensor hub core 206 includes distributor 250 to distribute sensor data streams to clients. If a client is configured to receive data as a batch, distributor 250 can distribute the sensor data stream to batch handler 260 for further compilation of the data into a batch of multiple input portions. Sensor clients 280 can include one or more clients, which can have the same or different frequency requirements for sensor data. Distributor 250 can provide the required data stream to the one or multiple clients. The data streams can be reconstructed data streams in accordance with what is described. Sensor hub core 206 includes a data scheduler that can be part of distributor 250 or separate from, but working together with, distributor 250. The scheduler is configured with the frequency requirements of each separate sensor client 280.

In one embodiment, sensor hub core 206 includes batch handler 260 to handle batch data streaming, which includes storing processed data into batch buffer 262. Batch buffer 262 represents a sensor core internal buffer to store batch data. In one embodiment, batch operation is based on a setting or configuration from a client 280, which allows the sensor hub to report data in batches. In one embodiment, the length of batch buffer 262 is an order of magnitude greater than the length of FIFO buffer 232. For example, batch buffer 262 can have a length of multiple hundreds or thousands of entries.

In one embodiment, signal reconstructor 240 of sensor hub core 206 includes batch filter 264 to apply filtering to batch data of batch buffer 262. In one embodiment, batch filter 264 operates in the batch sampling delay, and removes high frequency noise with low pass filtering. In one embodiment, batch filter 264 is or includes a FIR filter. As such, the mathematical expression set forth above with respect to FIFO filter 248 can also be applied by one embodiment of batch filter 264. It will be understood that a deep batch buffer 262, a very high order filter (e.g., higher than order 30) can be applied by batch filter 264. However, a filter of order 30 may be adequate for most implementations of system 200.

Sensor hub core 206 includes batch reporter 270 to distribute batch data to sensor clients 280. In one embodiment, batch reporter 270 monitors batch buffer 262 to determine when the buffer is full or has reach a client-defined delay requirement. When the threshold (either full buffer or client-specified threshold) has been reached, the filtered data can be distributed to the sensor client: check whether batch buffer is full or reached client delay requirement, if yes, distribute batch data to client.

Sensor hub core 206 includes arbitrator 290 to arbitrate frequency, FIFO length, batch delay settings, and/or other configuration from multiple sensor clients 280. Based on information and/or signals from arbitrator 290, driver 204 sets one or more sensor configurations 292 to apply to physical sensor 210 and/or sets one or more sensor sampling configuration settings. In one embodiment, sensor configuration 292 includes driver code that configures registers in physical sensor 210. Arbitrator 290 can configure both the sensor core interface and the physical sensor interface. In one embodiment, arbitrator 290 sets the maximum client frequency (MCF) based on requests from sensor clients 280. It will be understood that regardless of example frequencies provided below, each system setup and configuration can be different; thus, the examples below are meant to be illustrative and are not restrictive.

Figure 3:
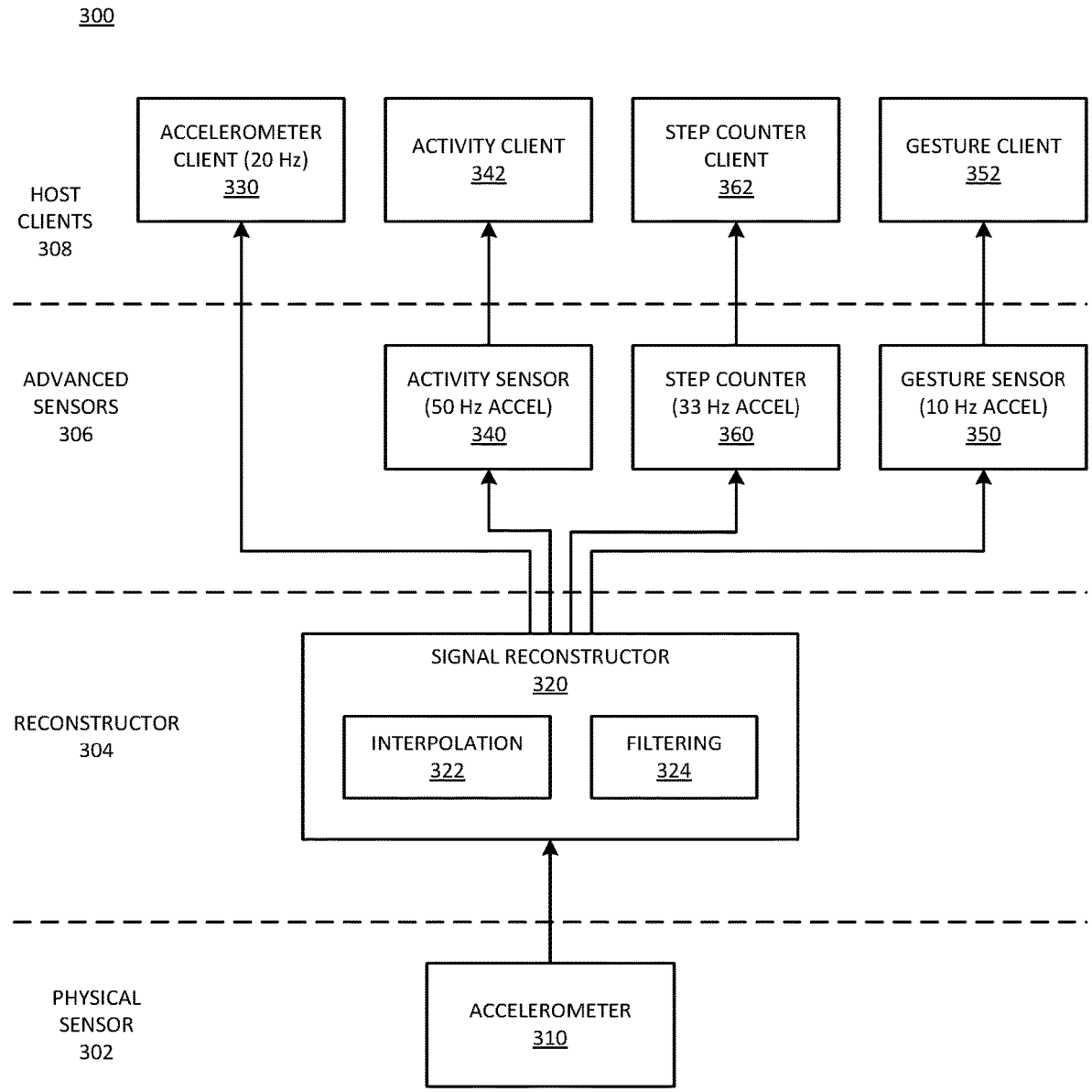
FIG. 3 is a block diagram of an embodiment of a system having clients corresponding to different frequencies.

FIG. 3 is a block diagram of an embodiment of a system having clients corresponding to different frequencies. System 300 illustrates elements of a sensor interface system, with physical sensor 302 that generates data, and host clients 308 as clients for the data. System 300 can include reconstructor 304 and advanced sensors 306 to interface host clients 308 to physical sensor 302. System 300 is one example of an embodiment of system 100. System 300 can be one example of an embodiment of system 200. In one embodiment, reconstructor 304 and advanced sensors 306 represent elements of the sensor hub core. In one embodiment, advanced sensors 306 represent virtual sensors, or sensor data streams based on physical sensor input, and processed to interpret the physical sensor data into different sensor information. Advanced sensors 306 utilize processed sensor data streams generated as reconstructed data by reconstructor 304.

In one embodiment, physical sensor 302 includes accelerometer 310. It will be understood that other sensor types could be used. System 300 includes a sensor hub (not explicitly shown) of which signal reconstructor 320 is a part. Signal reconstructor 320 receives data samples from accelerometer 310 and performs processing on the data prior to sending the data to the sensor clients. In one embodiment, signal reconstructor 320 performs interpolation 322 on data from accelerometer 310 for clients 302 that have different frequencies than a frequency at which system 300 operates accelerometer 310. Interpolation 322 can be any type of interpolation, and provides interpolated data from a raw data stream.

Examples of clients 308 and their associated frequencies can be as follows. Accelerometer client 330 has an associated frequency of 20 Hz. Activity client 342 has an associated frequency of 50 Hz, gesture client 352 has an associated frequency of 10 Hz, and step counter client 362 has an associated frequency of 33 Hz. For the example of system 300, assume that system 300 operates accelerometer 310 at a frequency of 50 Hz. For activity client 342, no interpolation 322 is needed, seeing that the sensor frequency and the sensor frequency match. However, for the other clients to receive accurate data at their requested frequencies without increasing the sampling rate of accelerometer 310, signal reconstructor 320 interpolates the raw sensor data and provides interpolated data streams of the appropriate frequency to each client.

It will be understood that all of clients 308 are ultimately clients of accelerometer 310, with different frequency settings. Advanced sensors 306 represent virtual sensors within the sensor hub that provide sensor data based on the data samples of the physical sensor, accelerometer 310. Signal reconstructor 320 can provide a 50 Hz data stream to activity sensor 340, which operates at 50 Hz accelerometer data. Based on interpolation 322, signal reconstructor 320 provides a 20 Hz data stream to accelerometer client 330, a 10 Hz accelerometer data stream to gesture sensor 350, and a 33 Hz accelerometer data stream to step counter 360. Each advanced sensor can further process the data and send it to an associated client.

In one embodiment, signal reconstructor 320 applies filtering 324. Filtering 324 can be any type of filtering described herein, as well as other types of filtering to remove noise from the raw sensor data and/or the interpolated sensor data. It will be understood that whereas signal reconstructor 320 does not need to interpolate the sensor data to provide to activity sensor 340, signal reconstructor 320 can still apply filtering 324 to reduce noise components of the data signal sent to activity sensor 340. Filtering 324 can include bandpass filtering (including low pass filtering) to reduce noise and/or enhance signal quality for a range of frequencies. In one embodiment, signal reconstructor 320 applies one or more types of filtering on one or more data streams for accelerometer client 330, activity sensor 340, gesture sensor 350, and/or step counter 360.

In one embodiment, an oscillator or other sampling control mechanism within the sensor hub of system 300 does not match evenly with any desired client frequency. For example, the sensor hub can include an oscillator that operates at a frequency of 46.9815 Hz, which does not divide evenly into any of 50 Hz, 33 Hz, 20 Hz, or 10 Hz. Assuming that the sensor clients require the exact frequency specified, in one embodiment, signal reconstructor 320 can perform interpolation 322 on all sensor data streams to provide the exact frequency desired. For an example, consider FIG. 5 and its discussion below.

Alternatively, each specified frequency can be understood to be a normalized frequency with respect to the oscillator of the sensor hub. For example, if the 46.9815 Hz oscillator signal is taken to be "50 Hz" for purposes of the system, the "10 Hz" signal can be a 9.3963 Hz signal, and the "20 Hz" signal can be an 18.7926 Hz signal, both normalized to the sensor hub oscillator. The normalization of the signals does not take away from the discussion of interpolation 322 providing the exact frequency requested by the sensor client. For example, a 46.9815 Hz (50 Hz) sampling can provide samples every 21.285 ms. A normalized 10 Hz client would request a sample be provided every 106.42 ms, while a normalized 20 Hz client would request a sample be provided every 53.212 ms. The 10 Hz client divides evenly (by 5) into the 50 Hz sampling, but the 20 Hz client does not divide into a whole integer (instead by 2.5). Thus, sampling for the 20 Hz client under traditional MCF methods would provide significant variations in sampling, with some samples varying more than 20% from the requested sampling rate based on providing the closest available samples.

Without interpolation 322, system 300 could not provide sampling frequency at perfect 20 Hz, 50 Hz, 100 Hz, or other frequency, but there would be an inherent instability. Such an inherent instability is due to sensor core process scheduling, undividable oscillator frequency, and/or other factors. Without interpolation 322, it would be expected that data distributed to clients 308 can only be done based on some subdivision of the raw sensor data, instead of at an exact frequency requested by the client. Additionally, application of filtering 324 is not known in traditional systems, and is unique to a signal reconstructor in accordance with an embodiment described herein.

Figure 4:
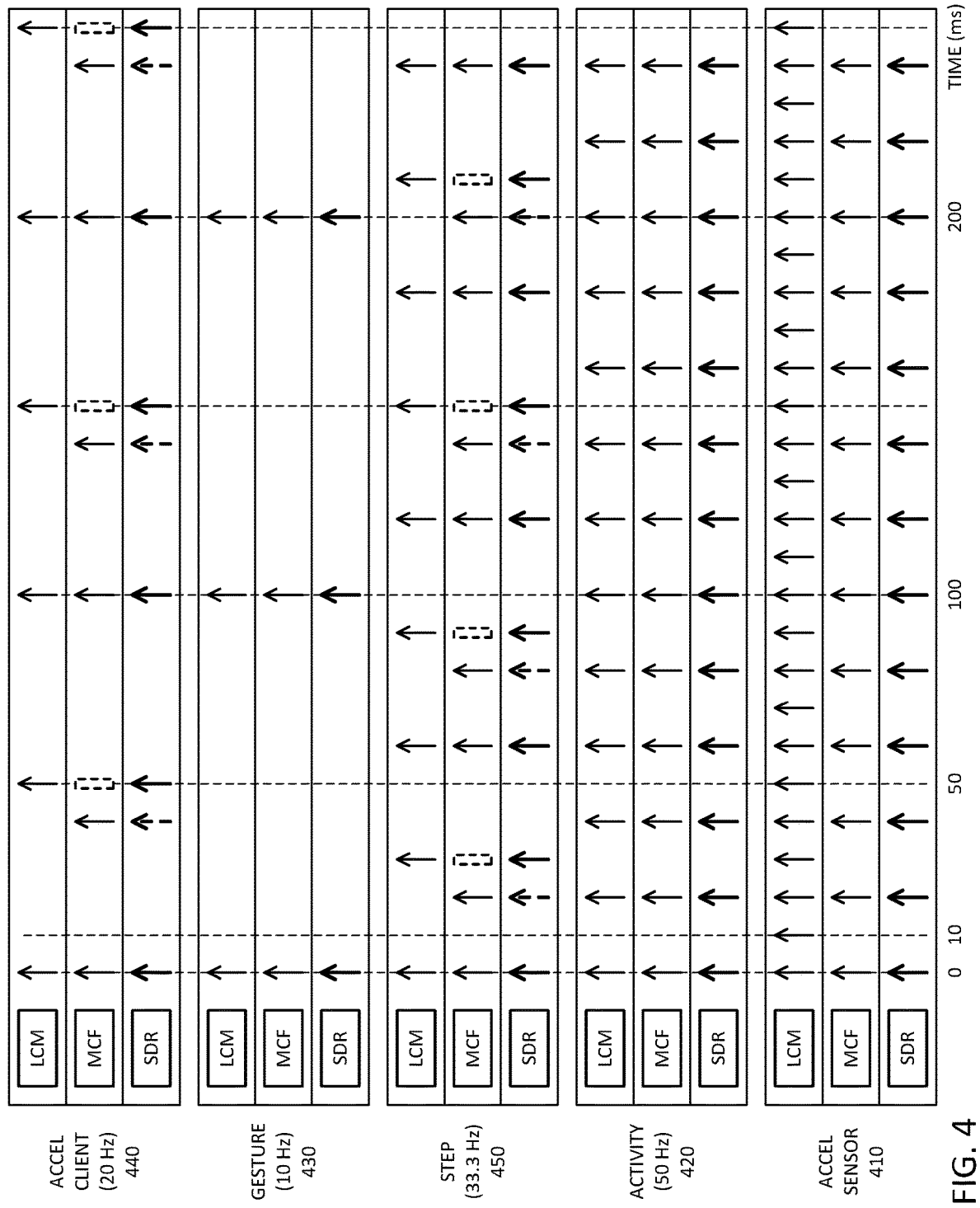
FIG. 4 is a diagrammatic representation of an embodiment of sensor clients that operate at different frequencies.

FIG. 4 is a diagrammatic representation of an embodiment of sensor clients that operate at different frequencies. Diagram 400 provides one example of a comparison of an LCM system, an MCF system, and a system that perform sensor data reconstruction. For each identified client, there is a box identifying the data corresponding to the LCM system as labeled "LCM," a box identifying the data corresponding to the MCF system as labeled "MCF," and a box identifying the data corresponding to the sensor data reconstruction system as labeled "SDR." Such data are shown next to each other for comparison purposes.

Diagram 400 illustrates examples of sensor clients that have corresponding frequencies. Activity client 420 has an associated frequency of 50 Hz. Gesture client 430 has an associated frequency of 10 Hz. Accelerometer client 440 has an associated frequency of 20 Hz. Step client 450 has an associated frequency of 33.3 Hz. It will be understood that the examples are illustrative, and other types of clients and sensors could be used. The identified clients could have different frequencies than what is illustrated.

In LCM, a sensor hub sets a physical sensor working at the least common multiple frequency of all clients, then downsamples the received data to the required frequency for each client. For purposes of example in diagram 400, accelerometer (Accel) client 410 is illustrated. The LCM of 20 Hz, 10 Hz, 33.3 Hz, and 50 Hz is 100 Hz. Thus, the system operates sensor 410 at 100 Hz, and there are multiple samples that will be generated and processed by the sensor core that will not be sent to any clients. It will be observed that there even in the small same of the diagram 400, there are several samples in sensor 410 for LCM that do not correspond to any of clients 420, 430, 440, or 450. While LCM can be observed to distribute corresponding samples or sampling events to each client in accordance with the desired frequencies, the system is not power efficient in such an implementation. With clients of different frequencies, the system can be configured to operate the physical sensor at a frequency much higher than any of the client frequencies, collecting far more data than needed by any of the clients.

In MCF, the sensor hub operate accelerometer sensor 410 at the MCF, which in the example of diagram 400 is 50 Hz (the frequency of activity client 420). It will be observed how the data for activity client 420 is aligned perfectly with the sampling of sensor 410, because it is assumed to be at the same frequency. Additionally, for gesture client 430 the data also aligns well because the requested 10 Hz divides evenly among every fifth 50 Hz sample. However, it will be observed that accelerometer client 440 and step client 450 receive samples or the sensor hub distributes data to them that is not aligned with the requested frequency. The solid arrows of the MCF solution represent the distributed samples. The dashed boxes represent the location where samples should be to align with the requested frequencies. Since the MCF does not have samples that match up with the desired frequency, the sensor hub distributes the nearest neighbor sample to each client.

Diagram 400 illustrates improvements provided by data interpolation in accordance with an embodiment of data reconstruction as described herein. In one embodiment, reconstruction operates sensor 410 at the maximum client frequency (MCF). Thus, in one embodiment, signal reconstruction is the same as MCF at sensor 410, as well as at activity client 420 and gesture client 430. However, whereas MCF illustrates dashed boxes where the data should be in accordance with desired frequencies but shows solid arrows where the actual distributed data is, signal reconstruction illustrates a dashed arrow where the sampling would occur, and shows a solid arrow to indicate the timing of the actual, reconstructed data sample. The reconstructed data sample is interpolated from collected data samples to determine an estimate of what the data value would be at the precise time of the requested sample. Thus, the sensor hub can maintain the client frequency exactly at the desired frequency for each individual client.

Figure 5:
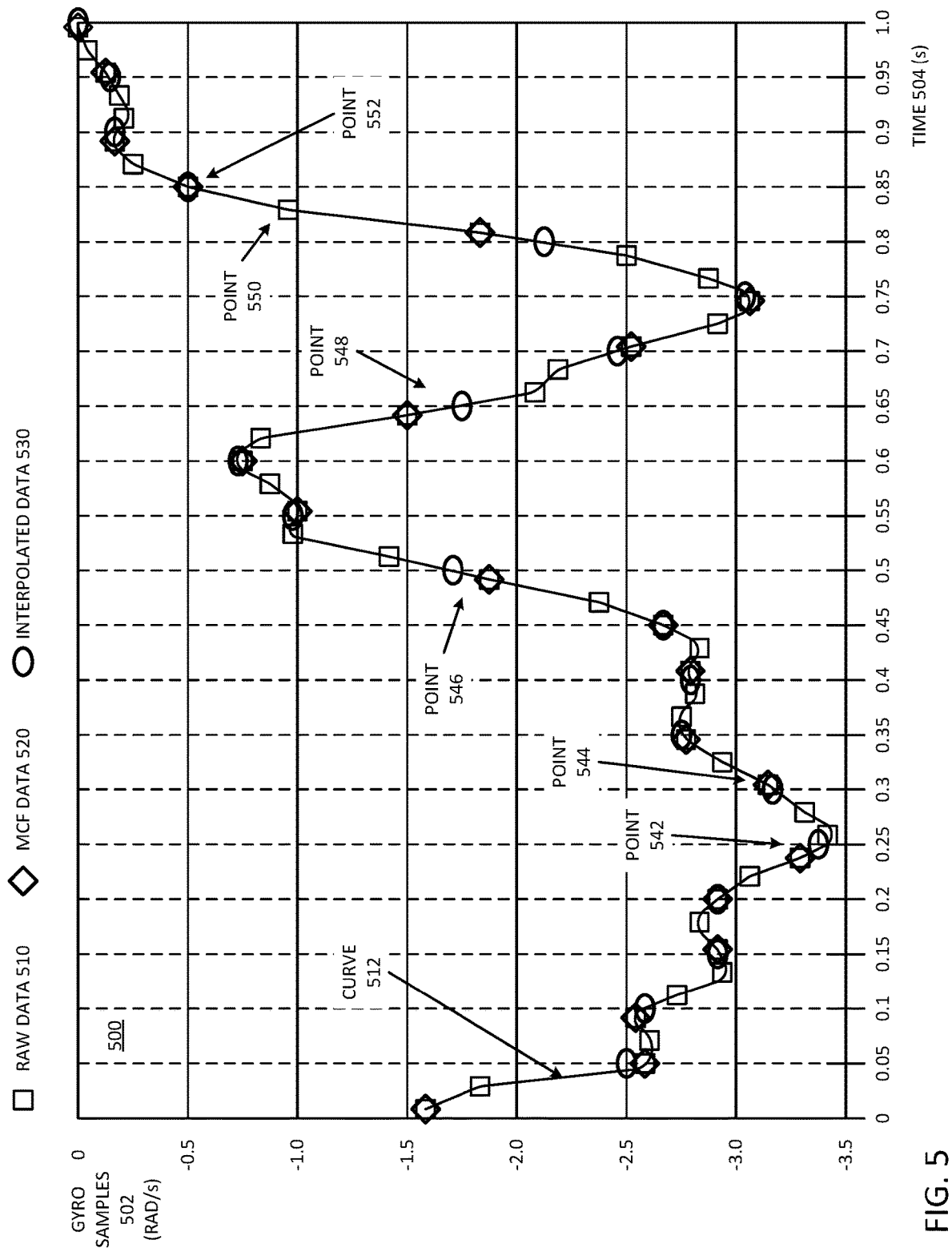
FIG. 5 is a diagrammatic representation of an embodiment of an operation of a sensor system with interpolation.

FIG. 5 is a diagrammatic representation of an embodiment of an operation of a sensor system with interpolation. Diagram 500 illustrates an example of data signal reconstruction versus MCF data on an estimated raw data curve. Diagram 500 can be data in accordance with any embodiment of system 100, system 200, and/or system 300. More specific to diagram 500, the data illustrates a plot of gyroscope samples 502 versus time 504. The gyroscope samples are measured in radians per second, while time is measured in seconds. Diagram 500 illustrates a curve of data across one second.

Curve 512 illustrates an estimation of the actual raw data curve, and may not perfectly match up with all points based on scaling. As illustrated in the legend, raw data 510 is represented by squares, MCF data 520 is represented by diamonds, and interpolated data 530 is represented by ovals. Similar to curve 512 possibly not matching perfectly with the data, the points on the curve represent actual test data, but may not completely accurately reflect the actual data due to scaling and simplification for purposes of illustrating diagram 500. Even if not a perfectly accurate representation diagram illustrates trends in the data that would be expected to be similar in any system if MCF data 520 were compared to interpolated data 530.

In one embodiment, raw data 510 has a setting of 50 Hz, but the actual frequency is 46.9815 Hz based on oscillator frequency of an oscillator within the sensor hub that implemented the tests. Thus, it will be understood that the oscillator frequency cannot divide into 50 Hz with no remainder. In the specific example, raw data 510 is 50 Hz data, and MCF data 520 and interpolated data 530 represent data for a 20 Hz data stream to a client that requests 20 Hz data. As a general observation, interpolated data 530 can provide precise 20 Hz data, but nearest neighbor frequency MCF data 520 varies significantly, from 15.15 Hz to 24.39 Hz. Thus, the values of data samples from MCF data 520 will be values selected from closest available samples, and the values of data samples from interpolated data 530 will be computed values.

Referring to specific points within diagram 500, the following can be observed. It will be understood that a 20 Hz signal stream will ideally have a data point every 0.05 seconds (1/20). It will also be understood that raw data 510 does not have sample points that align perfectly with the requested 20 Hz signal. As seen from the areas around points 542 and 544, it can be seen that interpolated data 530 provides samples (the ovals) right on 0.25 seconds and 0.30 seconds. However, raw data 510 has samples slightly before and after 0.25 seconds, and another sample slightly after 0.30 seconds. MCF data 520 tracks the raw data, with the sensor hub distributing data that is close to the desired timing, but not exactly. Whereas at point 544 the values of the samples are not significantly offset between MCF data 520 and interpolated data 530, the samples at point 542 are different. Namely, at point 542, the sample for MCF data 520 is offset nearly a tenth of a radian per second as compared to where the estimate raw data curve 512 actually crosses time 0.25. However, with interpolation, it will be observed that the sensor hub can provide interpolated data 530 with a point that is very close to the actual value of the raw data curve at time 0.25, and certainly much closer than the MCF sample.

Point 546 further illustrates the fact that interpolated data 530 provides a precise 20 Hz data stream to the client, whereas MCF data 520 varies significantly in both timing and value compared to the actual data curve 512. In addition to interpolation, in one embodiment, the sensor hub performs filtering on the data, which data can improve the accuracy of the sample and the quality of the data based on reducing noise. Point 548 further illustrates a significant accuracy difference between MCF data 520 and interpolated data 530, with the MCF sample being approximately 0.25 radians per second different than the actual data. In contrast, the interpolated data is close to the actual data at time 0.65 seconds.

Diagram 500 includes point 550 to illustrate that with an actual oscillator frequency of 46.9815 Hz, the sensor hub cannot provide actual 50 Hz data with no remainder. Point 552 illustrates the fact that for certain samples, the data for raw data 510, MCF data 520, and interpolated data 530 overlap exactly or almost exactly. However, interpolation can guarantee the desired 20 Hz signal, and provides good accuracy, while MCF data 520 cannot guarantee the desired frequency, and suffers from inaccuracy.

Figure 6:
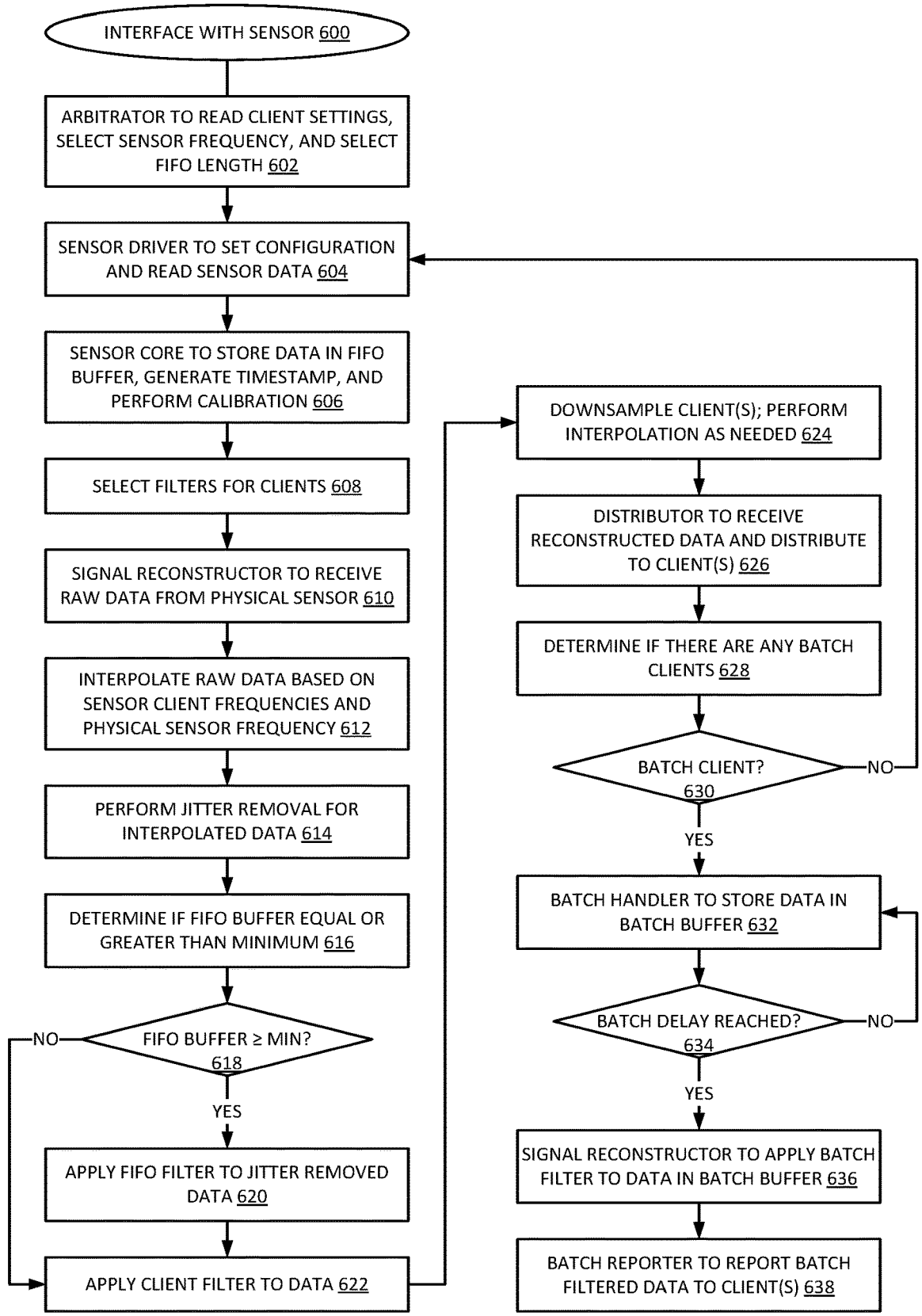
FIG. 6 is a flow diagram of an embodiment of a process for reconstructing a sensor signal in a sensor hub.

FIG. 6 is a flow diagram of an embodiment of a process for reconstructing a sensor signal in a sensor hub. Process 600 provides one example of interfacing with a sensor with interpolation and/or data signal filtering, in accordance with any embodiment described herein. Process 600 can be performed by a sensor hub that receives sensor data and processes it to provide it to the sensor clients. The physical sensor generates data in response to detecting changes to an environmental condition of the sensor device, such as with any sensor mentioned herein.

In one embodiment, an arbitrator of the sensor hub is to read client settings, select the sensor frequency, and select the FIFO length, 602. In one embodiment, the arbitrator can determine other settings than those identified. As running example throughout the description of process 600, consider three clients: one that requests 50 Hz data and a FIFO depth of 30, one that requests 20 Hz data and a FIFO length of 4, and one that requests 10 Hz data and a FIFO length of 10. It will be understood that the 50 Hz client has the highest requested frequency. In one embodiment, the arbitrator configures the sensor hub to operate the physical sensor at 50 Hz in accordance with the highest or maximum client frequency.

Regarding the depth or length of the FIFO, it will be understood that the shortest interval can be used to guarantee that the shortest timing is satisfied. Computing the requested delay for each client for data, it is observed that the 20 Hz client requests the shortest interval (($\frac{1}{10}$)*10=1.0>($\frac{1}{50}$)*30=0.6>($\frac{1}{20}$)*4=0.2). However, setting the operating frequency at 50 Hz means the sensor hub can set the FIFO input buffer to a longer length than 4, as computed by ($\frac{1}{20}$)*4=0.1=($\frac{1}{50}$)*10. Thus, in one embodiment, the sensor hub sets operation for 50 Hz with an input FIFO buffer of length 10.

Based on the determinations computed by the arbitrator, the sensor hub can cause the sensor driver to set configuration for the physical sensor, and read the sensor data in accordance with the computed settings, 604. In one embodiment, the sensor core is to store the input sensor data in a FIFO buffer, generate timestamp information for the data, and perform calibration of the data to align the data in time, 606. In one embodiment, the sensor hub determines one or more filters to apply for each of the associated sensor clients, 608. In one embodiment, the sensor hub selects different filtering for each different client.

In one embodiment, a signal reconstructor of the sensor hub is to receive the raw data from the physical sensor, 610, and interpolate the raw data based on the sensor client frequencies and operating frequency of the physical sensor, 612. In the specific example where the physical sensor is operated at 50 Hz, the sensor hub would perform interpolation on the raw sensor data to create interpolated 50 Hz data. In one embodiment, the signal reconstructor performs jitter removal on the interpolated data, 614, which in the example can be the 50 Hz interpolated data.

In one embodiment, the sensor hub determines if the FIFO buffer has reached a threshold, such as determining if the FIFO buffer is equal to or greater than the selected buffer length, 616. The selected buffer length is the length that provides the minimum delay requested for any of the clients, and can thus be referred to as a minimum (or min). If the FIFO buffer is greater than or equal to the min, 618 YES branch, in one embodiment, the signal reconstructor can apply a FIFO filter to the processed data, 620. For example, in accordance with the example, the sensor hub can perform jitter removal on the 50 Hz data, and then perform FIFO filtering on the 50 Hz jitter removed data. In one embodiment, such a filter can be an order 10 filter with a cutoff frequency normalized to 0.6 (which is consistent with the buffer length of 10, which is an order of filter matching the lowest order of filter that is acceptable for the system.

In one embodiment, the signal reconstructor applies a client filter to the data, 622. Based on process 600, the client filter can be applied in one of two scenarios: first, after performing the FIFO filtering on the jitter removed data; and, second, after performing the jitter removal, if the FIFO buffer is not greater than or equal to the min, 618 NO branch. The client filter is not necessarily performed in every case. Different filtering can be applied to data for different clients.

Referring again to the example, in one embodiment, the client filter can be an IIR filter applied for clients that will be downsampled from the 50 Hz interpolated data. Thus, the 50 Hz client may not have a client filter applied, in one embodiment. In one embodiment, the sensor hub applies an IIR filter of order 5, with a cutoff frequency normalized to 0.2 for the 10 Hz client. In one embodiment, the sensor hub applies an IIR filter of order 2, with a cutoff frequency normalized to 0.4 for the 20 Hz client. In one embodiment, the sensor hub downsamples the data for the specific clients to obtain a data stream that matches the requested frequency, 624. In one embodiment, the sensor hub interpolates the downsampled data as needed. A distributor of the sensor hub is to distribute data to the client. In accordance with the signal reconstructor, the distributor can receive the reconstructed data for delivery to one or more clients, 626.

In one embodiment, one or more clients are configured (e.g., via settings) to receive batch data. It will be understood that batch data is buffered data, and the incoming data from the physical sensor can already be buffered, as mentioned above. However, batch data refers to longer delays for receiving the sensor data, which can be multiple cycles of the input buffered data. Typically, a buffer for batch data is an order of magnitude longer or more than the input buffer. The distributor can determine if there are any batch clients, 628. If there are no batch clients, 630 NO branch, the distributor simply distributes the reconstructed data to the clients as mentioned above, and the system returns to monitoring the data from the sensor, as set forth starting at 604.

If there is one or more batch client, 630 YES branch, in one embodiment, the distributor sends the reconstructed data to a batch handler to store in a batch buffer, 632. There can be more than one batch delay for different clients configured for batch data. While the batch delay has not been reached, 634 NO branch, the batch handler will continue to receive and buffer the data in the batch buffer until a batch threshold is reached, 632. When the batch delay has been reached, 634 YES branch, in one embodiment, the signal reconstructor of the sensor hub is to apply one or more batch filters to the buffered batch data, 636. A batch reporter of the sensor hub reports the batch filtered data to the one or more batch clients, 638. After distribution of the batch data, the sensor hub can return to monitoring the data from the sensor, as set forth starting at 604.

Figure 7A:
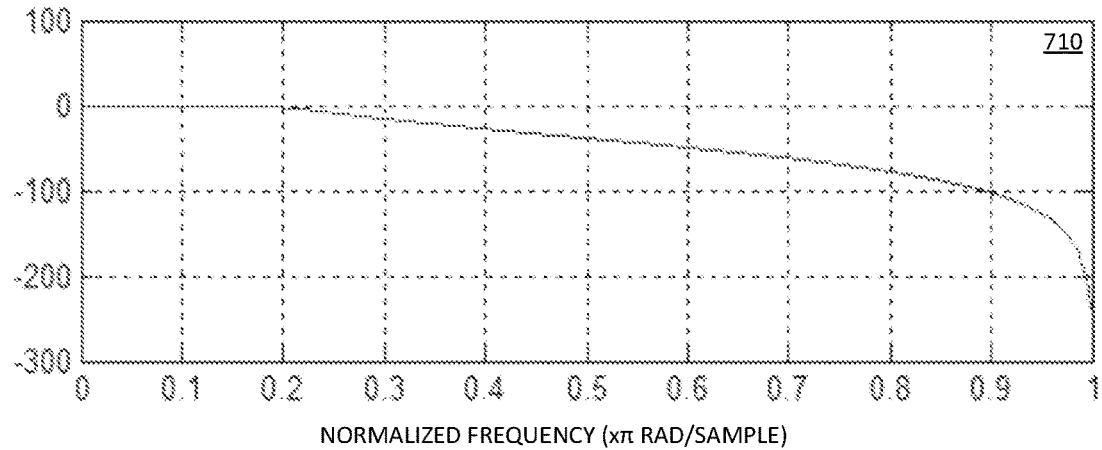
FIGS. 7A-7C are diagrammatic representations of filter responses for filters that can be applied in embodiments of sensor signal reconstruction.
Figure 7B:
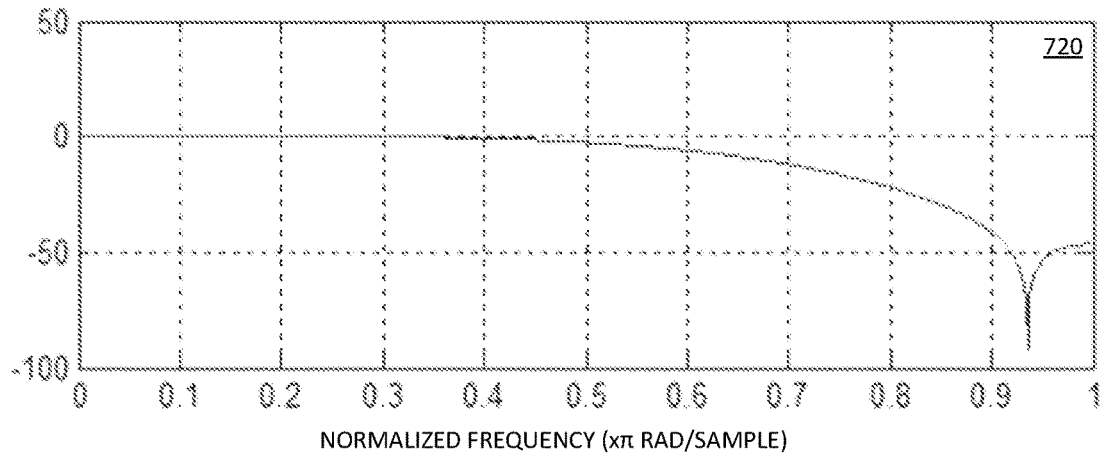
Figure 7C:
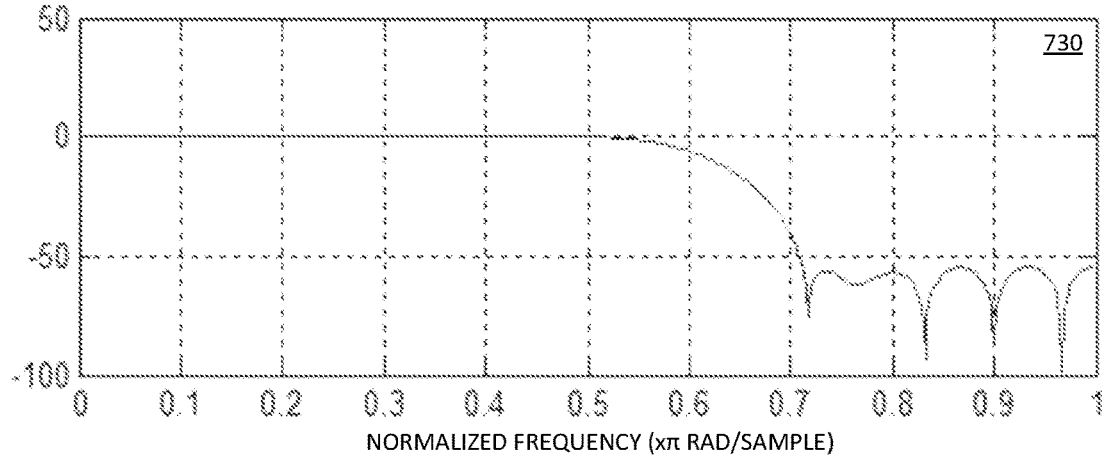

FIGS. 7A-7C are diagrammatic representations of filter responses for filters that can be applied in embodiments of sensor signal reconstruction. For the diagrammatic representations, it will be understood that each one plots magnitude in dB versus normalized frequency in radians per sample. Because the frequency is normalized, it can be expected that whatever frequency is selected as the MCF for a system, the filter behavior will be similar. Thus, for a system in accordance with many of the examples provided herein, where 50 Hz sampling is described for the operation of the physical sensor, the filter behaviors are expected to be the same or similar to those shown whether a higher or lower frequency is used.

When referring to filtering, it will be understood that filtering can account for the Nyquist sampling law, where filtering frequencies can be selected based on the desired data. The Nyquist sampling law indicates that information cannot exceed f/2, where f is the sampling frequency. For example, human motion has a practical limit of approximately 15 Hz of information. Frequencies higher than 15 Hz are not likely to carry information regarding human motion. Thus, a client configured to monitor human motion could request a 30 Hz sensor data stream. Consequently, for a sensor requesting a data stream of 30 Hz sensor data, the system can filter frequencies below approximately 15 Hz, seeing that a 30 Hz signal only contains frequency information for 15 Hz and below. Similarly, a client requesting 20 Hz sensor data can only be requesting information of 10 Hz or lower, and higher frequencies can be determined to be noise and filtered out or removed. It will be understood that in addition to the examples provided, other types of filtering can be used to remove higher frequency information. Additionally, filtering DC (direct current) information can also be performed.

Referring to FIG. 7A, diagram 710 illustrates one example of an IIR filter response for FIFO data. The specific filter plotted was an order 4 filter with a cutoff frequency of 0.2 (normalized). Other orders and cutoff frequencies can be applied to affect the falloff and the position of the knee. Referring to FIG. 7B, diagram 720 illustrates one example of a FIR filter response for FIFO data. The specific filter plotted was an order 10 filter with a cutoff frequency of 0.6 (normalized). Other orders and cutoff frequencies can be applied to affect the falloff and the position of the knee and asymptote. Referring to FIG. 7C, diagram 730 illustrates one example of a FIR filter response for batch data. The specific filter plotted was an order 30 filter with a normalized cutoff frequency of 0.6. Other orders and cutoff frequencies can be applied to affect the falloff and the position of the primary knee and asymptotes.

FIG. 8A is a diagrammatic representation of a graph of test data for a gyroscope of a system including a sensor hub that performs sensor signal reconstruction. Diagram 802 illustrates one example of test data for testing signal reconstruction in a system receiving data from a gyroscope sensor device. More specifically, a mobile phone device was test by first rotating the phone on a table 180 degrees along a Z axis, and then rotating the phone back to the starting position. The sensor was operated at 50 Hz, based on an oscillator on the sensor hub that provided data closer to 47 Hz. Diagram 802 represents activity as indicated by gyroscope data readings 814 (measured in radians per second) over time 812 (measured in seconds). The first rotation appears as activity starting at approximately 5 seconds, and the second rotation appears as activity starting at approximately 15 seconds. The data of diagram 802 serves as the basis for table 820 of FIG. 8B and table 840 of FIG. 8C.

Referring to FIG. 8B, table 820 provides one example of experimental results for one embodiment of a system that performs sensor signal reconstruction. The data for table 820 refers to static noise, in which the system computed the standard deviation of the gyroscope output over a period of time as the device is still on a table. For the static noise test, the first four seconds of data from table 802 were used to compute the static noise. The data for table 840 refers to integration results, in which the system computed the integration of the gyroscope output over a period of time as a user rotated the device during test.

Table 820 includes row 822, which is the raw data stream at 47 Hz received from the gyroscope. The static noise indication serves as a baseline of 0.101 degrees per second (deg/s). The other rows of data are compared against the baseline. Row 824 illustrates a 50 Hz data stream representing MCF data, as would be obtained through a traditional MCF implementation. It will be observed that the static noise decrease is minimal to 0.100 deg/s, for a reduction of 1%, which is not statistically significant. Row 826 illustrates a 50 Hz data stream representing interpolated data without filtering. Even without filtering, interpolation of the 47 Hz raw sensor data to the 50 Hz client signal reduced static noise to 0.084 deg/s, for a reduction of approximately 17.3%.

Row 828 illustrates a 50 Hz data stream representing interpolated data that is then filtered with a client filter, which can be an IIR filter applied during a buffering delay. In one embodiment, a client filter is applied during a downsampling delay, but there is no downsampling delay when the data is not downsampled. In one embodiment, such a delay can be applied during a different delay in the data path of data from the sensor to the client. The client filter resulted in static noise of 0.048 deg/s, for a reduction of approximately 52.5%.

Row 830 illustrates a 50 Hz data stream representing interpolated data that is then filtered with a FIFO filter, which can be a FIR filter. The FIFO filter resulted in static noise of 0.070 deg/s, for a reduction of approximately 30.7%. Row 832 illustrates a 50 Hz data stream representing interpolated data that is then filtered with a batch filter, which can be a FIR filter. The batch filter resulted in static noise of 0.070 deg/s, for a reduction of approximately 30.5%. It will be understood that the numbers are rounded to significant digits, resulting the different of approximate reduction between the FIFO filter and the batch filter.

It will be observed from table 820 that the client filter noise is the smallest. Such a result can be expected for static noise, seeing that for the filtering applied, the client filter had a cutoff frequency of 5 Hz, which was a smaller cutoff than either the FIFO or batch filtering. Interpolation alone provided a measurable benefit in the results, which interpolation plus filtering showed further improved results.

Referring to FIG. 8C, table 840 provides one example of experimental results for one embodiment of a system that performs sensor signal reconstruction. Table 820 shows the gyroscope data integration test results, in which integration over all 50 seconds of the test data of diagram 802 was computed by the system. Table 840 includes row 842, which is the raw data stream at 47 Hz received from the gyroscope. The integration result of −2.32 serves as a baseline for comparison to the other rows of data. It will be understood that the drift in time is computed as an absolute value with reference to the baseline.

Row 844 illustrates a 20 Hz data stream representing traditional MCF data in which the sensor hub ignored timestamp information. It will be observed that the integration result was 4.65, for a drift in time of 0.58 degrees per minute (deg/min). Essentially, there was a significant amount of drift. Row 826 illustrates a 20 Hz data stream representing traditional MCF data in which the sensor hub accounted for timestamp information. It will be observed that the integration result was −1.66, for a drift in time of 0.06 deg/min. Without considering timestamp information, the integration result drifts rapidly. The drift is less significant when considering timestamp information for MCF.

Row 848 illustrates a 20 Hz data stream representing interpolated data without additional filtering. The integration result for the interpolated data was −1.90, which has a drift in time of 0.04 deg/min relative to the baseline raw data. Thus, interpolation alone provides an advantage over the MCF data. Row 850 illustrates a 20 Hz data stream representing interpolated data that is then filtered with a client filter, which can be an IIR filter applied to the data. The client filter resulted in an integration result of −2.63, for a drift in time of 0.03 deg/min. Row 852 illustrates a 20 Hz data stream representing interpolated data that is then filtered with a FIFO filter, which can be a FIR filter. The FIFO filter resulted in an integration result of −2.10, for a drift in time of 0.02 deg/min. Row 854 illustrates a 20 Hz data stream representing interpolated data that is then filtered with a batch filter, which can be a FIR filter. The batch filter resulted in an integration result of 0.03 deg/min, for a drift in time of 0.03 deg/min.

Figure 9A:
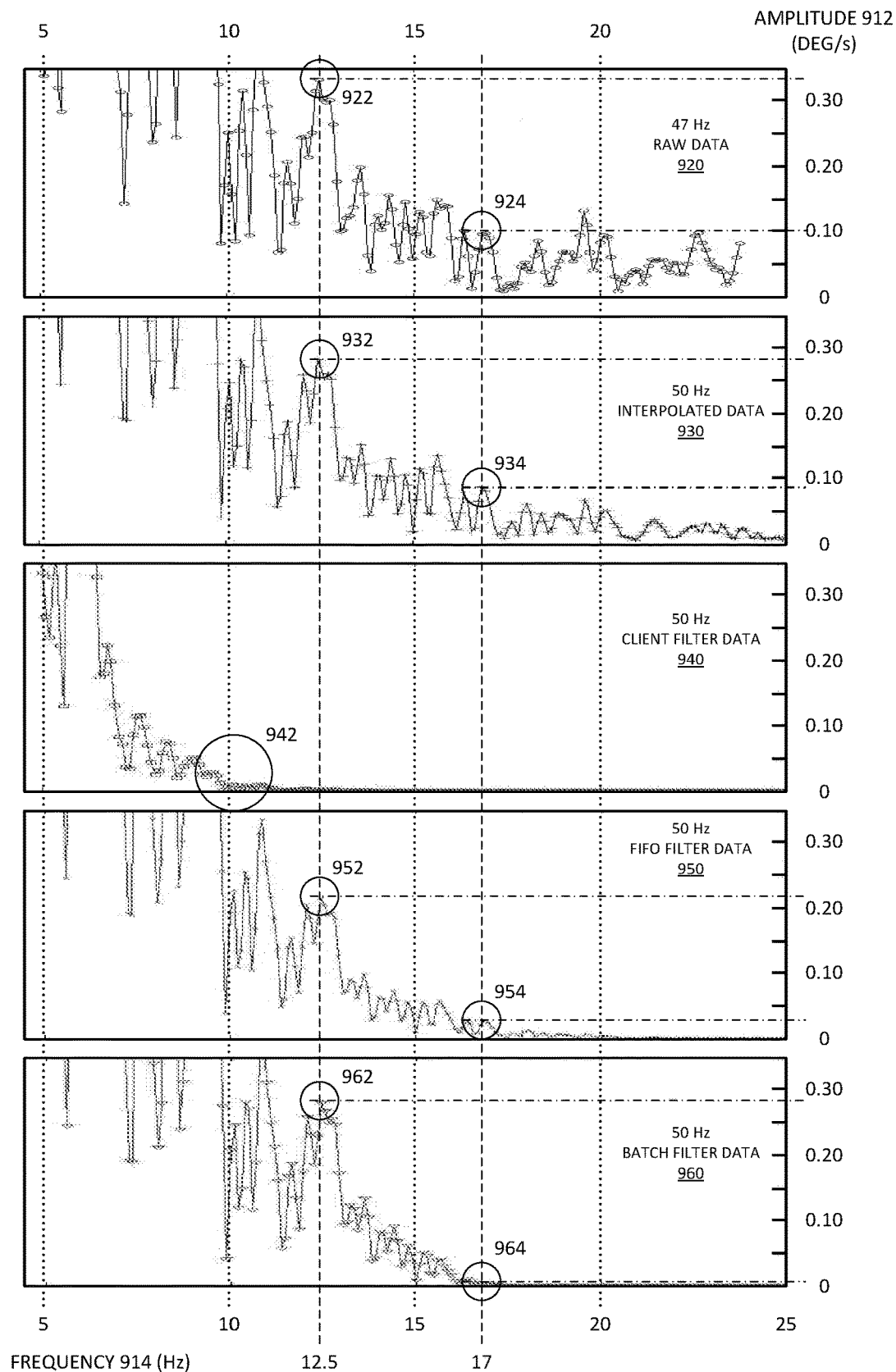
FIG. 9A illustrates diagrammatic representations of sensor signal data as modified in one embodiment of sensor hub signal reconstruction.

FIG. 9A illustrates diagrammatic representations of sensor signal data as modified in one embodiment of sensor hub signal reconstruction. A test system generated a Fast Fourier Transform (FFT) on each of 5 signals: 1) a 47 Hz raw data, as represented in graph 920; 2) a 50 Hz interpolated data stream (interpolated from the 47 Hz raw data), as represented in graph 930; 3) the interpolated data stream as filtered by a client filter, as represented in graph 940; 4) the interpolated data stream as filtered by a FIFO filter, as represented in graph 950; and, 5) the interpolated data stream as filtered by a batch filter, as represented in graph 960. In one embodiment, each additional stage of filtering is processed on the previously filtered data. Thus, for example, the sensor hub can perform interpolation, and then apply a client filter to the interpolated data, and then apply a FIFO filter to the client filtered data, and so forth.

The test that generated the data for the graphs had 10.24 seconds of input data from a 46.9185 Hz gyroscope raw data. For the test, a sensor hub applied linear interpolation on the ~47 Hz gyroscope raw data to generate a perfect 50 Hz sensor data stream. The sensor hub applied an IIR client filter with order 4 and a cutoff frequency of 5 Hz to the 50 Hz sensor data stream (for a 10 Hz client). The selection of a 10 Hz client is for illustration only and is not limiting. The selection of a 10 Hz client provides significant, observable differences in the filtered data compared to the raw data, as set out below. The sensor hub applied a FIR FIFO filter with order 10 and a cutoff frequency of 15 Hz to the 50 Hz sensor data stream. The sensor hub applied a FIR batch filter with order 30 and a cutoff frequency of 15 Hz to the 50 Hz sensor data stream. The delays introduced by above 3 filters were, respectively, 0.04 s, 0.1 s, and 0.3 s. These delay already existed in sensor hub downsampling, FIFO buffering, and batch processing. Thus, the delays introduced by the three filters were applied during the existing delay, which resulted in no additional delay from the filtering processing.

Each graph 920, 930, 940, 950, and 960 is positioned along the same x-axis, and with its own y-axis. All y-axes are to scale. Thus, each graph illustrates amplitude 912 against frequency 914. Amplitude 912 is measured in degrees per second, and frequency 914 is measured in Hertz. It will be observed that the graphs do not include frequency information before 5 Hz. In the testing, none of the data illustrated results of interest in the range of 0-5 Hz for the discussion here. The graphs are plotted on separate y-axes to be able to distinguish the different curves from each other. The graphs are plotted on the same x-axis to illustrate general trends that can be observed from the data.

Graph 940 illustrates how the applied client filter removed noise above 10 Hz, and reduces the signal above 5 Hz. For a 10 Hz client, signal information above 5 Hz is not needed. It will be observed at segment 942 (the circle) that the client filter essentially removes any signal component above approximately 10 Hz. Graphs 920, 930, 950, and 960 each include two circled graph segments, which illustrate points of comparison at approximately 12.5 Hz and approximately 17 Hz, as labeled along frequency 914.

Points 924, 934, 954, and 964 correspond to the signals at approximately 17 Hz. As seen at point 924 with graph 920, the raw sensor data has a peak of approximately 0.10 deg/s at 17 Hz. As seen at point 934 with graph 930, interpolation offers somewhat better high frequency performance, given that the peak in the interpolated data is slightly lower (approximately 0.8 deg/s). Continuing to 20 Hz in graphs 920 and 930, it will be observed that interpolation reduces the high frequency components of the raw data above 15 Hz, but the high frequency noise suppression is small. Referring to graph 950, the FIFO filter reduces noise above 15 Hz. As seen at point 954, the 17 Hz peak is approximately less than 0.03 deg/s. Referring to graph 960, the batch filter further reduces noise above 15 Hz. As seen at point 964, the 17 Hz peak is nearly eliminated, meaning higher frequency content is better suppressed.

If frequencies above 15 Hz are considered undesired noise, frequencies below 15 Hz can be considered desired signal information. Thus, application of the filters would ideally suppress frequencies greater than 15 Hz, while not suppressing signal components below 15 Hz. Referring to point 922 of graph 920, there is a peak at approximately 12.5 Hz, which has an amplitude greater than 0.30 deg/s in the raw data. Referring to graph 930, point 932 illustrates that the interpolation does reduce the 12.5 Hz peak somewhat, but the amplitude is just a little lower than 0.30 deg/s. It will be observed from graph 950 that the FIFO filter had an undesired effect on the signal data. At point 952 it will be observed that the 12.5 Hz peak has been reduced to a little above 0.20 deg/s. The order of the FIFO filter is small, which results in some negative impact on the lower frequency signal. The order of the batch filter is higher, and thus while it can be observed from graph 960 that the higher frequency components are significantly suppressed, the lower frequency components are not significantly reduced. As seen at point 962, the amplitude of the 12.5 Hz peak is just slightly lower than the peak in the interpolated data. Thus, it can be seen that all filtering performed offer some advantage, and the batch filtering provided the best filtering performance.

Figure 9B:
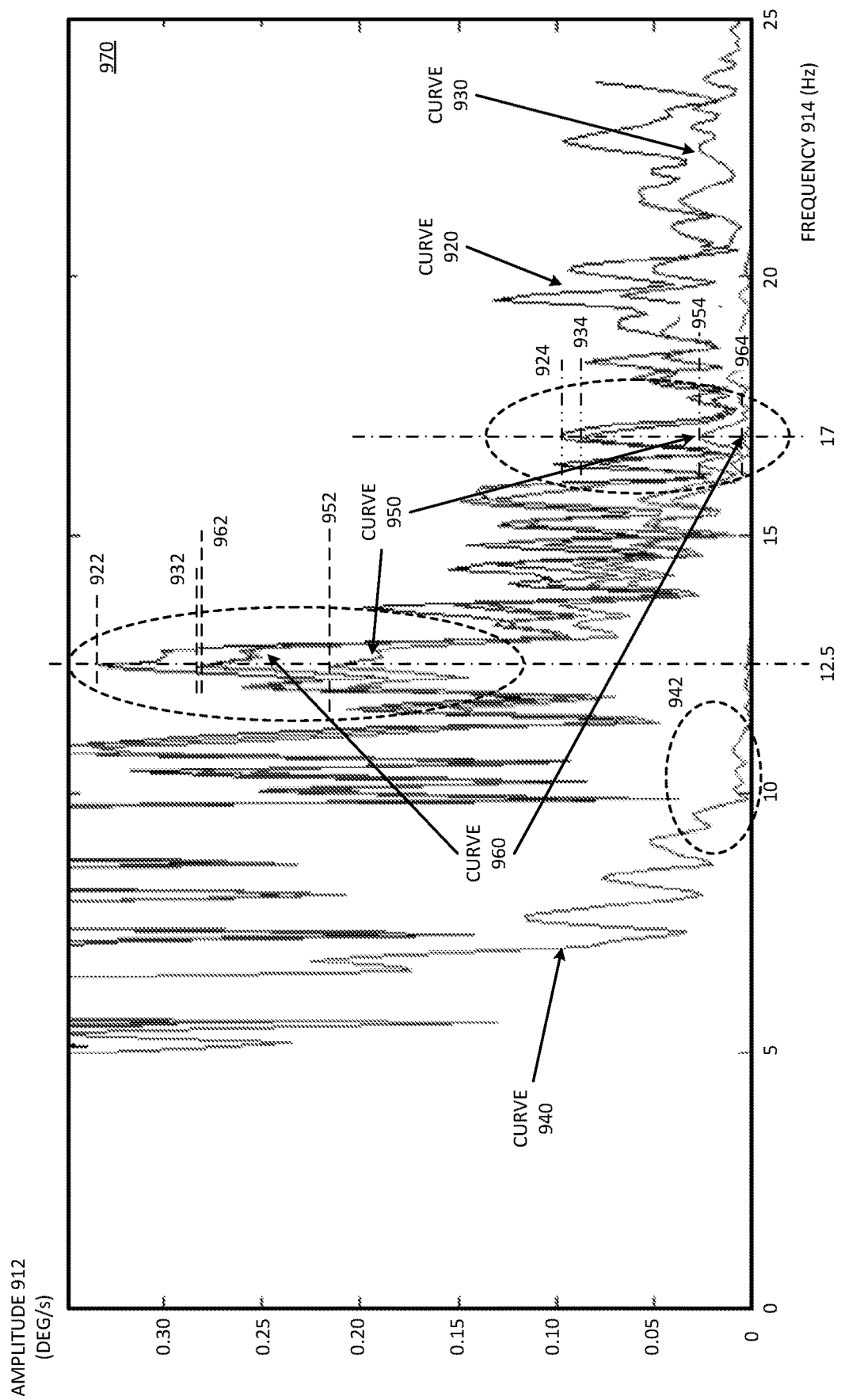
FIG. 9B is a diagrammatic representation of a composite graph of the sensor signal data of FIG. 9A as modified in one embodiment of sensor hub signal reconstruction.

FIG. 9B is a diagrammatic representation of a composite graph of the sensor signal data of FIG. 9A as modified in one embodiment of sensor hub signal reconstruction. Diagram 970 illustrates test data comparing the signal response for various data streams based on an original raw sensor data signal generated by a sensor device. Diagram 970 represents data stream amplitude 912 measured in degrees per second over frequency 914 measured in Hertz, showing a composite of curves corresponding to graphs 920, 930, 940, 950, and 960 of FIG. 9A. The curves of diagram 970 are each labeled with a respective reference number corresponding to a graph of FIG. 9A.

The test data of diagram 970 follows various assumptions. One assumption is that humans cannot produce motion data in frequencies above approximately 15 Hz. Thus, in a system based on tracking motion of a user-carried device, the signal reconstructor can filter frequencies above 15 Hz. Another assumption is that based on the Nyquist sampling rule, a client requesting data at frequency f only wants information at frequency f/2. Thus, for each client requesting data at frequency f, the signal reconstructor can apply a low pass filter with a cutoff frequency of f/2. Additionally, if the sensor data is to be downsampled to frequency f, the low pass filter with cutoff frequency f/2 can be applied to the downsampled signal without loss of information for the client. Thus, for example, for a 20 Hz client, sensor data sampled at 50 Hz can be downsampled to 20 Hz, interpolated, and filtered with a cutoff frequency of 10 Hz without loss of data for the client.

While certain details of diagram 970 may be obscured in providing a composite of the data stream graphs, the general trends pointed out above can be observed as a comparison of noise reduction in the FFT signals. Diagram 970 includes curve 920 illustrating the 47 Hz raw data, curve 930 illustrating the 50 Hz interpolated data stream, curve 940 illustrating the interpolated data stream as filtered by the client filter, curve 950 illustrating the interpolated data stream as filtered by the FIFO filter, and curve 960 illustrating the interpolated data stream as filtered by the batch filter.

Diagram 970 includes the same graph segment points from FIG. 9A for comparison purposes. It will be observed with reference to point 942 that curve 940 suppresses signal components above approximately 10 Hz. With reference to the segment at approximately 12.5 Hz, it will be observed that in the signal portion of the data stream (less than 15 Hz), interpolation curve 930 somewhat reduces the signal component as seen at point 932. The peak of curve 960 at point 962 can be observed to be only slightly lower than that of the interpolated data for the batch filtering. The peak of curve 950 at point 952 illustrates the reduction of the signal component in the FIFO filtering.

With reference to the approximately 17 Hz segment of diagram 970 (higher frequency components, or non-signal information), comparing points 924 and 934 illustrates that interpolation curve 930 offers slightly better performance as compared to raw data curve 920. Point 954 illustrates even further high frequency suppression for FIFO filter curve 950. Point 964 illustrates even further high frequency suppression for batch filter curve 960.

Figure 10:
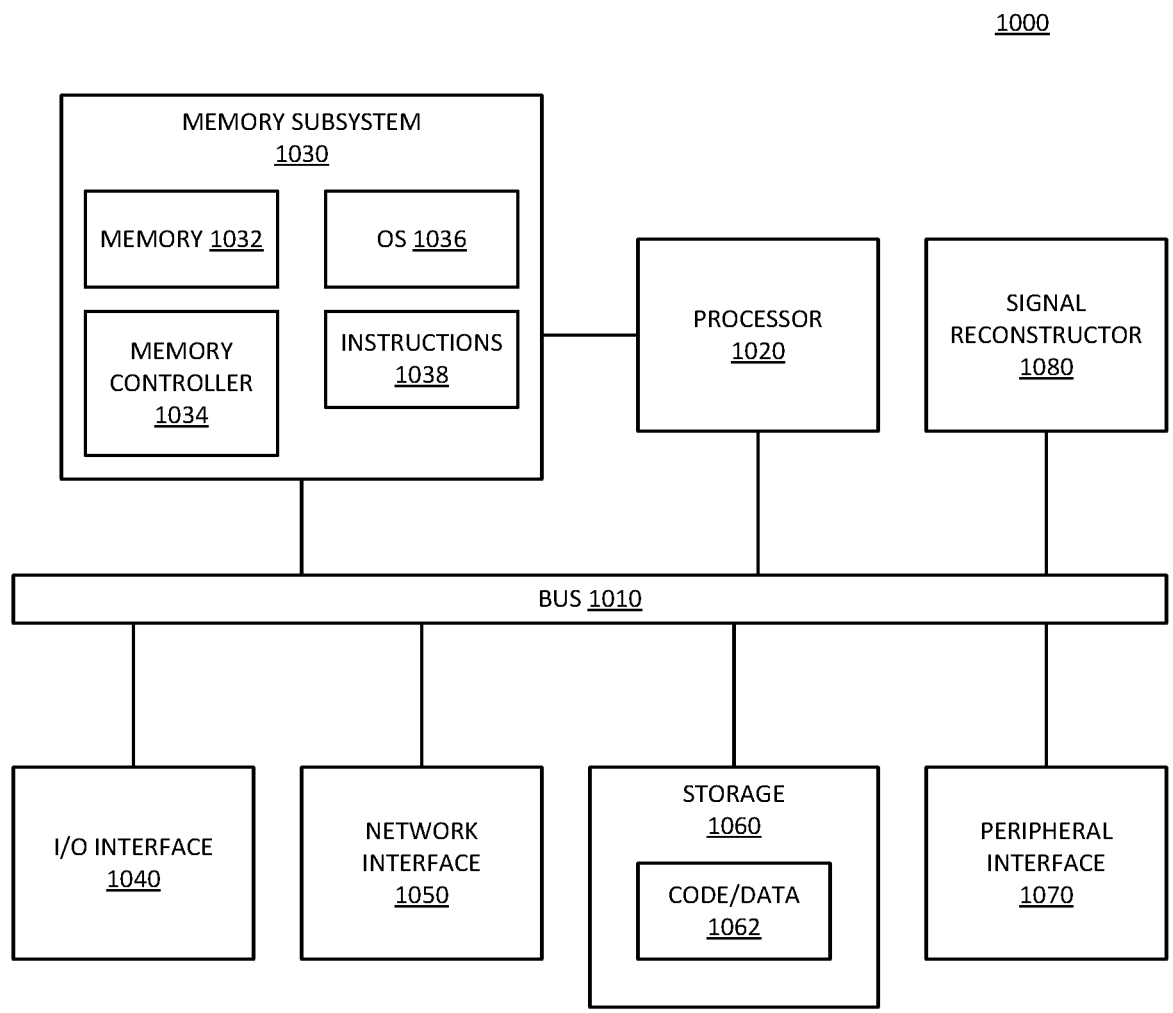
FIG. 10 is a block diagram of an embodiment of a computing system in which sensor signal reconstruction can be implemented.

FIG. 10 is a block diagram of an embodiment of a computing system in which sensor signal reconstruction can be implemented. System 1000 represents a computing device in accordance with any embodiment described herein, and can be a laptop computer, a desktop computer, a server, a gaming or entertainment control system, a scanner, copier, printer, routing or switching device, or other electronic device. System 1000 includes processor 1020, which provides processing, operation management, and execution of instructions for system 1000. Processor 1020 can include any type of microprocessor, central processing unit (CPU), processing core, or other processing hardware to provide processing for system 1000. Processor 1020 controls the overall operation of system 1000, and can be or include, one or more programmable general-purpose or special-purpose microprocessors, digital signal processors (DSPs), programmable controllers, application specific integrated circuits (ASICs), programmable logic devices (PLDs), or the like, or a combination of such devices.

Memory subsystem 1030 represents the main memory of system 1000, and provides temporary storage for code to be executed by processor 1020, or data values to be used in executing a routine. Memory subsystem 1030 can include one or more memory devices such as read-only memory (ROM), flash memory, one or more varieties of random access memory (RAM), or other memory devices, or a combination of such devices. Memory subsystem 1030 stores and hosts, among other things, operating system (OS) 1036 to provide a software platform for execution of instructions in system 1000. Additionally, other instructions 1038 are stored and executed from memory subsystem 1030 to provide the logic and the processing of system 1000. OS 1036 and instructions 1038 are executed by processor 1020. Memory subsystem 1030 includes memory device 1032 where it stores data, instructions, programs, or other items. In one embodiment, memory subsystem includes memory controller 1034, which is a memory controller to generate and issue commands to memory device 1032. It will be understood that memory controller 1034 could be a physical part of processor 1020.

Processor 1020 and memory subsystem 1030 are coupled to bus/bus system 1010. Bus 1010 is an abstraction that represents any one or more separate physical buses, communication lines/interfaces, and/or point-to-point connections, connected by appropriate bridges, adapters, and/or controllers. Therefore, bus 1010 can include, for example, one or more of a system bus, a Peripheral Component Interconnect (PCI) bus, a HyperTransport or industry standard architecture (ISA) bus, a small computer system interface (SCSI) bus, a universal serial bus (USB), or an Institute of Electrical and Electronics Engineers (IEEE) standard 1394 bus (commonly referred to as "Firewire"). The buses of bus 1010 can also correspond to interfaces in network interface 1050.

System 1000 also includes one or more input/output (I/O) interface(s) 1040, network interface 1050, one or more internal mass storage device(s) 1060, and peripheral interface 1070 coupled to bus 1010. I/O interface 1040 can include one or more interface components through which a user interacts with system 1000 (e.g., video, audio, and/or alphanumeric interfacing). In one embodiment, I/O interface 1040 can include a high definition (HD) display that provides an output to a user. High definition can refer to a display having a pixel density of approximately 100 PPI (pixels per inch) or greater, and can include formats such as full HD (e.g., 1080p), retina displays, 4K (ultra high definition or UHD), or others. High definition can also refer to projected displays (e.g., head-mounted displays) that have comparable visual quality to pixel displays. Network interface 1050 provides system 1000 the ability to communicate with remote devices (e.g., servers, other computing devices) over one or more networks. Network interface 1050 can include an Ethernet adapter, wireless interconnection components, USB (universal serial bus), or other wired or wireless standards-based or proprietary interfaces.

Storage 1060 can be or include any conventional medium for storing large amounts of data in a nonvolatile manner, such as one or more magnetic, solid state, or optical based disks, or a combination. Storage 1060 holds code or instructions and data 1062 in a persistent state (i.e., the value is retained despite interruption of power to system 1000). Storage 1060 can be generically considered to be a "memory," although memory 1030 is the executing or operating memory to provide instructions to processor 1020. Whereas storage 1060 is nonvolatile, memory 1030 can include volatile memory (i.e., the value or state of the data is indeterminate if power is interrupted to system 1000).

Peripheral interface 1070 can include any hardware interface not specifically mentioned above. Peripherals refer generally to devices that connect dependently to system 1000. A dependent connection is one where system 1000 provides the software and/or hardware platform on which operation executes, and with which a user interacts.

In one embodiment, system 1000 includes signal reconstructor 1080, which enables signal reconstruction in accordance with any embodiment described herein. In one embodiment, signal reconstructor 1080 is part of a sensor hub of processor 1020, and interfaces with one or more sensors (not explicitly shown) that provide monitored or measured data to the processor. Signal reconstructor 1080 generates reconstructed sensor data to send to one or more sensor clients (not specifically shown) that execute on processor 1020, instead of sending raw sensor data to the clients. In one embodiment, signal reconstructor 1080 performs interpolation on the raw sensor data to provide frequency-aligned data streams. The frequency alignment refers to generating data streams having frequencies matching the one or more sensor clients. In one embodiment, signal reconstructor 1080 applies one or more filtering processing operations on the sensor data.

Figure 11:
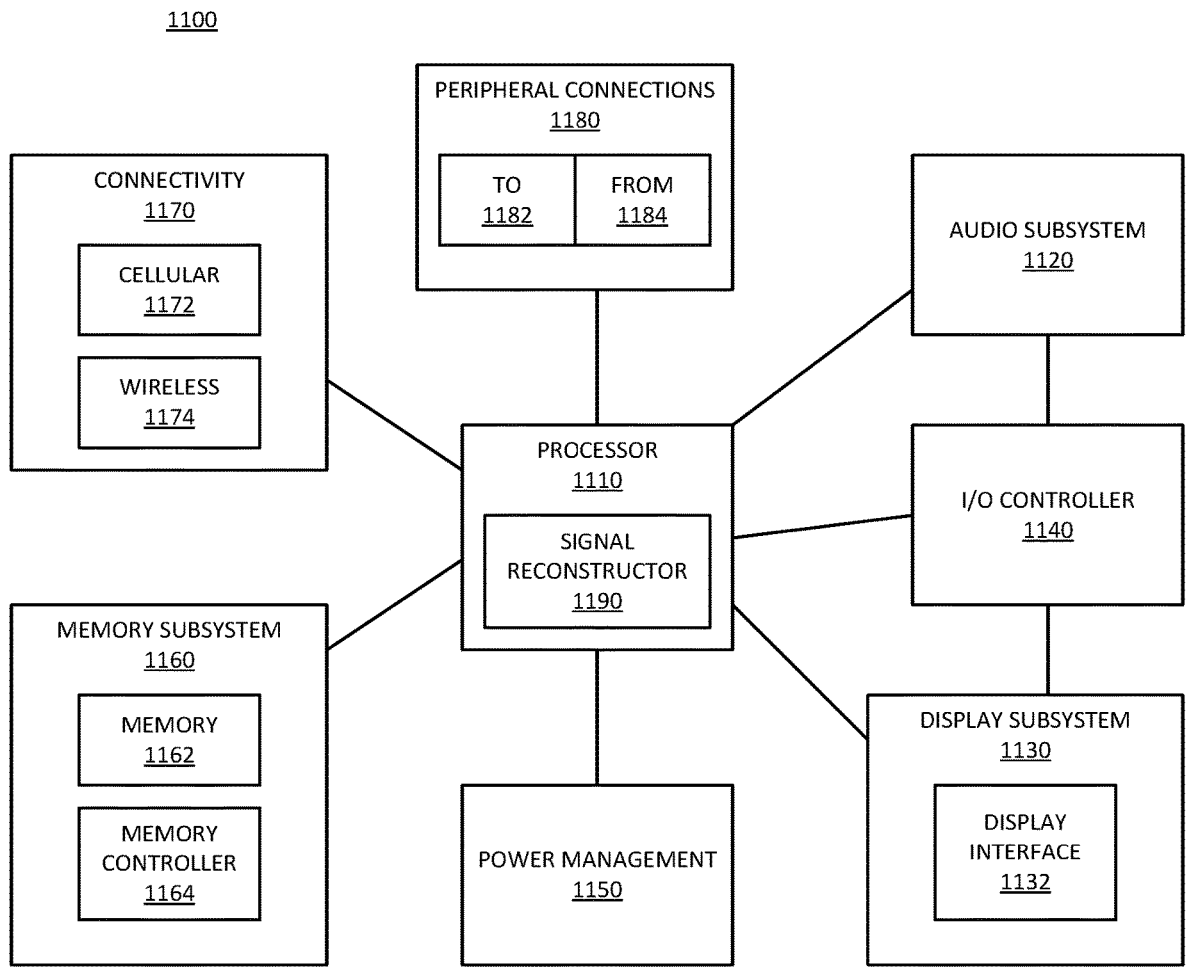
FIG. 11 is a block diagram of an embodiment of a device in which sensor signal reconstruction can be implemented.

FIG. 11 is a block diagram of an embodiment of a device in which sensor signal reconstruction can be implemented. Device 1100 represents a mobile computing device, such as a laptop, computing tablet, a wireless-enabled e-reader, a mobile phone or smartphone, smart watch, fitness monitor or other wearable user monitor, wearable computing device, or other device. It will be understood that certain of the components are shown generally, and not all components of such a device are shown in device 1100. Not all devices will necessarily include all components shown.

Device 1100 includes processor 1110, which performs the primary processing operations of device 1100. Processor 1110 can include one or more physical devices, such as microprocessors, application processors, microcontrollers, programmable logic devices, or other processing means. The processing operations performed by processor 1110 include the execution of an operating platform or operating system on which applications and/or device functions are executed. The processing operations include operations related to I/O (input/output) with a human user or with other devices, operations related to power management, and/or operations related to connecting device 1100 to another device. The processing operations can also include operations related to audio I/O and/or display I/O.

In one embodiment, device 1100 includes audio subsystem 1120, which represents hardware (e.g., audio hardware and audio circuits) and software (e.g., drivers, codecs) components associated with providing audio functions to the computing device. Audio functions can include speaker and/or headphone output, as well as microphone input. Devices for such functions can be integrated into device 1100, or connected to device 1100. In one embodiment, a user interacts with device 1100 by providing audio commands that are received and processed by processor 1110.

Display subsystem 1130 represents hardware (e.g., display devices) and software (e.g., drivers) components that provide a visual and/or tactile display for a user to interact with the computing device. Display subsystem 1130 includes display interface 1132, which includes the particular screen or hardware device used to provide a display to a user. In one embodiment, display interface 1132 includes logic separate from processor 1110 to perform at least some processing related to the display. In one embodiment, display subsystem 1130 includes a touchscreen device that provides both output and input to a user. In one embodiment, display subsystem 1130 includes a high definition (HD) display that provides an output to a user. High definition can refer to a display having a pixel density of approximately 100 PPI (pixels per inch) or greater, and can include formats such as full HD (e.g., 1080p), retina displays, 4K (ultra high definition or UHD), or others.

I/O controller 1140 represents hardware devices and software components related to interaction with a user. I/O controller 1140 can operate to manage hardware that is part of audio subsystem 1120 and/or display subsystem 1130. Additionally, I/O controller 1140 illustrates a connection point for additional devices that connect to device 1100 through which a user might interact with the system. For example, devices that can be attached to device 1100 might include microphone devices, speaker or stereo systems, video systems or other display device, keyboard or keypad devices, or other I/O devices for use with specific applications such as card readers or other devices.

As mentioned above, I/O controller 1140 can interact with audio subsystem 1120 and/or display subsystem 1130. For example, input through a microphone or other audio device can provide input or commands for one or more applications or functions of device 1100. Additionally, audio output can be provided instead of or in addition to display output. In another example, if display subsystem includes a touchscreen, the display device also acts as an input device, which can be at least partially managed by I/O controller 1140. There can also be additional buttons or switches on device 1100 to provide I/O functions managed by I/O controller 1140.

In one embodiment, I/O controller 1140 manages devices such as accelerometers, cameras, light sensors or other environmental sensors, gyroscopes, global positioning system (GPS), or other hardware that can be included in device 1100. The input can be part of direct user interaction, as well as providing environmental input to the system to influence its operations (such as filtering for noise, adjusting displays for brightness detection, applying a flash for a camera, or other features). In one embodiment, device 1100 includes power management 1150 that manages battery power usage, charging of the battery, and features related to power saving operation.

Memory subsystem 1160 includes memory device(s) 1162 for storing information in device 1100. Memory subsystem 1160 can include nonvolatile (state does not change if power to the memory device is interrupted) and/or volatile (state is indeterminate if power to the memory device is interrupted) memory devices. Memory 1162 can store application data, user data, music, photos, documents, or other data, as well as system data (whether long-term or temporary) related to the execution of the applications and functions of system 1100. In one embodiment, memory subsystem 1160 includes memory controller 1164 (which could also be considered part of the control of system 1100, and could potentially be considered part of processor 1110). Memory controller 1164 includes a scheduler to generate and issue commands to memory device 1162.

Connectivity 1170 includes hardware devices (e.g., wireless and/or wired connectors and communication hardware) and software components (e.g., drivers, protocol stacks) to enable device 1100 to communicate with external devices. The external device could be separate devices, such as other computing devices, wireless access points or base stations, as well as peripherals such as headsets, printers, or other devices.

Connectivity 1170 can include multiple different types of connectivity. To generalize, device 1100 is illustrated with cellular connectivity 1172 and wireless connectivity 1174. Cellular connectivity 1172 refers generally to cellular network connectivity provided by wireless carriers, such as provided via GSM (global system for mobile communications) or variations or derivatives, CDMA (code division multiple access) or variations or derivatives, TDM (time division multiplexing) or variations or derivatives, LTE (long term evolution—also referred to as "4G"), or other cellular service standards. Wireless connectivity 1174 refers to wireless connectivity that is not cellular, and can include personal area networks (such as Bluetooth), local area networks (such as WiFi), and/or wide area networks (such as WiMax), or other wireless communication. Wireless communication refers to transfer of data through the use of modulated electromagnetic radiation through a non-solid medium. Wired communication occurs through a solid communication medium.

Peripheral connections 1180 include hardware interfaces and connectors, as well as software components (e.g., drivers, protocol stacks) to make peripheral connections. It will be understood that device 1100 could both be a peripheral device ("to" 1182) to other computing devices, as well as have peripheral devices ("from" 1184) connected to it. Device 1100 commonly has a "docking" connector to connect to other computing devices for purposes such as managing (e.g., downloading and/or uploading, changing, synchronizing) content on device 1100. Additionally, a docking connector can allow device 1100 to connect to certain peripherals that allow device 1100 to control content output, for example, to audiovisual or other systems.

In addition to a proprietary docking connector or other proprietary connection hardware, device 1100 can make peripheral connections 1180 via common or standards-based connectors. Common types can include a Universal Serial Bus (USB) connector (which can include any of a number of different hardware interfaces), DisplayPort including MiniDisplayPort (MDP), High Definition Multimedia Interface (HDMI), Firewire, or other type.

In one embodiment, system 1100 includes signal reconstructor 1190, which enables signal reconstruction in accordance with any embodiment described herein. In one embodiment, signal reconstructor 1190 is part of a sensor hub of processor 1110, and interfaces with one or more sensors (not explicitly shown) that provide monitored or measured data to the processor. Signal reconstructor 1190 generates reconstructed sensor data to send to one or more sensor clients (not specifically shown) that execute on processor 1110, instead of sending raw sensor data to the clients. In one embodiment, signal reconstructor 1190 performs interpolation on the raw sensor data to provide frequency-aligned data streams. The frequency alignment refers to generating data streams having frequencies matching the one or more sensor clients. In one embodiment, signal reconstructor 1190 applies one or more filtering processing operations on the sensor data.

In one aspect, a sensor interface circuit includes: an I/O (input/output) interface to couple to a sensor device and receive data from the sensor device; a processor to process the data when received from the sensor device, including to perform signal reconstruction on the data, the signal reconstruction including interpolation of data values to generate interpolated data for multiple different sensor clients configured to receive the data at different respective frequencies; and send the processed data to the multiple clients in accordance with the different respective frequencies.

In one embodiment, the I/O interface is to couple to one or more of an accelerometer, a gyroscope, a magnetometer, a barometer, a temperature sensor, a humidity sensor, a light sensor, or a heart rate sensor. In one embodiment, the processor is to receive data from the sensor device at approximately a highest frequency of the different frequencies configured for the multiple clients. In one embodiment, the processor is to operate the sensor device at a frequency that does not divide evenly into one or more of the different frequencies. In one embodiment, the processor is further to filter the received data prior to the processor to send the processed data to the multiple clients. In one embodiment, the processor it to apply a jitter removal filter to the received data. In one embodiment, the processor is to filter the received data during a buffering delay configured in a data path to the multiple clients, to avoid introduction of delay by the filtering. In one embodiment, the processor is to apply a client filter during a downsampling delay. In one embodiment, the processor is to apply a finite input response filter during an input buffering delay. In one embodiment, the processor is to apply a finite input response filter during a batch buffering delay. In one embodiment, the processor is to apply different filters to the received data for different clients, and send data to different clients corresponding to specific filters for the clients. In one embodiment, the processor includes multiple versions of a filter, and is further to select a version of the filter based on a configuration of the I/O interface.

In one aspect, an electronic device with a sensor circuit includes: a sensor device to generate data based on sensing a change in an environmental condition of the sensor device; and a sensor hub coupled to the sensor device, to receive the data from the sensor device, the sensor hub including a processor to process the data when received from the sensor device, including to perform signal reconstruction on the data including interpolation of data values to generate interpolated data for multiple different sensor clients configured to receive the data at different respective frequencies; and send the processed data to the multiple clients in accordance with the different respective frequencies. In one aspect, the electronic device with any embodiment of the sensor interface circuit.

In one aspect, a method for interfacing with a sensor includes: receiving data from a sensor device at a sensor hub, the data based on detected changes to an environmental condition of the sensor device; processing the received data at the sensor hub prior to providing the data to multiple sensor clients configured to receive the sensor data at different frequencies; wherein the processing includes performing signal reconstruction on the received data including interpolating data values to generate interpolated data for the multiple sensor clients at the different frequencies; and sending the processed data to the multiple client in accordance with the different respective frequencies.

In one embodiment, the sensor device comprises one or more of an accelerometer, a gyroscope, a magnetometer, a barometer, a temperature sensor, a humidity sensor, a light sensor, or a heart rate sensor. In one embodiment, receiving the data comprises receiving data from the sensor device at approximately a highest frequency of the different frequencies configured for the multiple clients. In one embodiment, the sensor device is to operate at a frequency that does not divide evenly into one or more of the different frequencies. In one embodiment, processing the received data comprises filtering the received data prior to the processor to send the processed data to the multiple clients. In one embodiment, processing the received data comprises applying a jitter removal filter to the received data. In one embodiment, processing the received data comprises filtering the received data during a buffering delay configured in a data path to the multiple clients, to avoid introduction of delay by the filtering. In one embodiment, processing the received data comprises applying a client filter during a downsampling delay. In one embodiment, processing the received data comprises applying a finite input response filter during an input buffering delay. In one embodiment, the processing the received data comprises applying a finite input response filter during a batch buffering delay. In one embodiment, processing the received data comprises applying different filters to the received data for different clients, and send data to different clients corresponding to specific filters for the clients. In one embodiment, processing further comprises selecting one of multiple versions of a filter based on a configuration of the I/O interface.

In one aspect, an article of manufacture comprising a computer readable storage medium having content stored thereon, which when accessed causes a sensor hub to execute operations to perform a method for interfacing with a sensor in accordance with any of the method claims. In one aspect, an apparatus for interfacing with a sensor comprising means for executing operations to perform a method in accordance with any of the method claims.

Flow diagrams as illustrated herein provide examples of sequences of various process actions. The flow diagrams can indicate operations to be executed by a software or firmware routine, as well as physical operations. In one embodiment, a flow diagram can illustrate the state of a finite state machine (FSM), which can be implemented in hardware and/or software. Although shown in a particular sequence or order, unless otherwise specified, the order of the actions can be modified. Thus, the illustrated embodiments should be understood only as an example, and the process can be performed in a different order, and some actions can be performed in parallel. Additionally, one or more actions can be omitted in various embodiments; thus, not all actions are required in every embodiment. Other process flows are possible.

To the extent various operations or functions are described herein, they can be described or defined as software code, instructions, configuration, and/or data. The content can be directly executable ("object" or "executable" form), source code, or difference code ("delta" or "patch" code). The software content of the embodiments described herein can be provided via an article of manufacture with the content stored thereon, or via a method of operating a communication interface to send data via the communication interface. A machine readable storage medium can cause a machine to perform the functions or operations described, and includes any mechanism that stores information in a form accessible by a machine (e.g., computing device, electronic system, etc.), such as recordable/non-recordable media (e.g., read only memory (ROM), random access memory (RAM), magnetic disk storage media, optical storage media, flash memory devices, etc.). A communication interface includes any mechanism that interfaces to any of a hardwired, wireless, optical, etc., medium to communicate to another device, such as a memory bus interface, a processor bus interface, an Internet connection, a disk controller, etc. The communication interface can be configured by providing configuration parameters and/or sending signals to prepare the communication interface to provide a data signal describing the software content. The communication interface can be accessed via one or more commands or signals sent to the communication interface.

Various components described herein can be a means for performing the operations or functions described. Each component described herein includes software, hardware, or a combination of these. The components can be implemented as software modules, hardware modules, special-purpose hardware (e.g., application specific hardware, application specific integrated circuits (ASICs), digital signal processors (DSPs), etc.), embedded controllers, hardwired circuitry, etc.

Besides what is described herein, various modifications can be made to the disclosed embodiments and implementations of the invention without departing from their scope. Therefore, the illustrations and examples herein should be construed in an illustrative, and not a restrictive sense. The scope of the invention should be measured solely by reference to the claims that follow.

What is claimed is:

1. A sensor interface circuit, comprising:
I/O (input/output) interface hardware to couple to a sensor device and receive sensor data from the sensor device;
a processor to
process the sensor data received from the sensor device, including to perform signal reconstruction on the sensor data, the signal reconstruction including interpolation of data values to generate interpolated data for multiple different sensor clients configured to receive the sensor data at different respective frequencies, the interpolated data compatible with the different respective frequencies;
filter the sensor data during a buffering delay configured in a data path to the multiple different sensor clients, to avoid introduction of delay by the filtering; and
send the processed sensor data to the multiple sensor clients in accordance with the different respective frequencies, wherein the processor is to filter the sensor data prior to the processor to send the processed sensor data to the multiple sensor clients.

2. The sensor interface circuit of claim 1, wherein the I/O interface hardware is to couple to one or more of an accelerometer, a gyroscope, a magnetometer, a barometer, a temperature sensor, a humidity sensor, a light sensor, or a heart rate sensor.

3. The sensor interface circuit of claim 1, wherein the processor is to receive data from the sensor device at approximately a highest frequency of the different frequencies configured for the multiple sensor clients.

4. The sensor interface circuit of claim 1, wherein the processor is to operate the sensor device at a frequency that does not divide evenly into one or more of the different frequencies.

5. The sensor interface circuit of claim 1, wherein the processor it to apply a jitter removal filter to the sensor data.

6. The sensor interface circuit of claim 1, wherein the processor is to apply a client filter during a downsampling delay.

7. The sensor interface circuit of claim 1, wherein the processor is to apply a finite input response filter during an input buffering delay.

8. The sensor interface circuit of claim 1, wherein the processor is to apply a finite input response filter during a batch buffering delay.

9. The sensor interface circuit of claim 1, wherein the processor is to apply different filters to the sensor data for different sensor clients, and send data to the different sensor clients corresponding to specific filters for the different sensor clients.

10. The sensor interface circuit of claim 1, wherein the processor includes multiple versions of a filter, and is further to select a version of the filter based on a configuration of the I/O interface.

11. An electronic device with a sensor circuit, comprising:
a sensor device to generate sensor data based on sensing a change in an environmental condition of the sensor device; and
a sensor hub coupled to the sensor device, to receive the sensor data from the sensor device, the sensor hub including a processor to
process the sensor data received from the sensor device, including to perform signal reconstruction on the sensor data, including interpolation of data values to generate interpolated data for multiple different sensor clients configured to receive the sensor data at different respective frequencies, the interpolated data compatible with the different respective frequencies;
filter the sensor data during a buffering delay configured in a data path to the multiple different sensor clients, to avoid introduction of delay by the filtering; and
send the processed sensor data to the multiple different sensor clients in accordance with the different respective frequencies, wherein the processor is to filter the sensor data prior to the processor to send the processed sensor data to the multiple different sensor clients.

12. The electronic device of claim 11, wherein the sensor device is to operate at a frequency that does not divide evenly into any of the different frequencies of the multiple sensor clients.

13. The electronic device of claim 11, wherein the processor to filter the sensor data prior to the processor to send the processed sensor data to the multiple different sensor clients, comprises the processor to apply one or more of: a jitter removal filter, an infinite input response filter during a downsampling delay, a finite input response filter during an input buffering delay, or a finite input response filter during a batch buffering delay, or a combination.

14. A method for interfacing with a sensor, comprising:
receiving sensor data from a sensor device at a sensor hub, the sensor data based on detected changes to an environmental condition of the sensor device;
processing the sensor data at the sensor hub prior to providing the sensor data to multiple sensor clients configured to receive the sensor data at different frequencies;
wherein the processing includes performing signal reconstruction on the sensor data, including interpolating data values to generate interpolated data for multiple sensor clients at the different frequencies, the interpolated data compatible with the different frequencies;
wherein the processing includes filtering the sensor data during a buffering delay configured in a data path to the multiple different sensor clients, to avoid introduction of delay by the filtering; and
sending the sensor data to the multiple sensor clients in accordance with the different frequencies, prior to sending the processed data to the multiple sensor clients.

15. The method of claim 14, wherein receiving sensor data from the sensor device comprises receiving sensor data from one or more of an accelerometer, a gyroscope, a magnetometer, a barometer, a temperature sensor, a humidity sensor, a light sensor, or a heart rate sensor.

16. The method of claim 14, wherein receiving sensor data from the sensor device comprises receiving the sensor data at approximately a highest frequency of the different frequencies configured for the multiple sensor clients.

17. The method of claim 14, wherein filtering the sensor data prior to sending the processed sensor data to the multiple sensor clients includes applying one or more of: a jitter removal filter, an infinite input response filter during a downsampling delay, a finite input response filter during an input buffering delay, or a finite input response filter during a batch buffering delay, or a combination.

18. The method of claim 14, wherein filtering the sensor data comprises applying different filters to the received data for different clients, and sending the processed sensor data to the different sensor clients corresponding to specific filters for the different sensor clients.

* * * * *